United States Patent
Macoviak et al.

(10) Patent No.: US 6,669,680 B1
(45) Date of Patent: *Dec. 30, 2003

(54) METHODS OF MAINTAINING SELECTIVE FLOW WITHIN A VESSEL

(76) Inventors: John Macoviak, 5412 Thunderbird La., La Jolla, CA (US) 92037; Wilfred Samson, 19369 Farwell Ave., Saratoga, CA (US) 95070

( * ) Notice: Subject to any disclaimer, the term of this patent is extended or adjusted under 35 U.S.C. 154(b) by 0 days.

This patent is subject to a terminal disclaimer.

(21) Appl. No.: 09/564,281

(22) Filed: May 4, 2000

Related U.S. Application Data

(63) Continuation of application No. 09/378,676, filed on Aug. 20, 1999
(60) Provisional application No. 60/116,836, filed on Jan. 22, 1999.

(51) Int. Cl.⁷ .............................................. A61M 31/00
(52) U.S. Cl. ........................................ 604/509; 604/43
(58) Field of Search ..................... 604/43, 6.16, 500, 604/506–510, 93.01, 96.01, 103.01–103.04, 264, 523, 524, 532

(56) References Cited

U.S. PATENT DOCUMENTS

| | | | |
|---|---|---|---|
| 3,435,824 A | * 4/1969 | Gamponia | 604/264 |
| 4,712,551 A | * 12/1987 | Rayhanabad | 128/334 |
| 5,308,320 A | * 5/1994 | Safar et al. | 604/4 |
| 5,458,574 A | * 10/1995 | Machold et al. | 604/101 |
| 5,599,329 A | * 2/1997 | Gabbay | 604/284 |
| 6,086,557 A | * 7/2000 | Morejohn et al. | 604/500 |
| 6,258,120 B1 | 7/2001 | McKenzie | |

* cited by examiner

*Primary Examiner*—Manuel Mendez
(74) *Attorney, Agent, or Firm*—Fulwider Patton Lee & Utecht, LLP

(57) ABSTRACT

The invention is a catheter with a fluid flow divider positioned near the distal end of the catheter for dividing a first lumen into two channels at a point where a second lumen branches from the first lumen, and for selectively perfusing the branch lumen. The invention is particularly suited for use in the aortic arch. The fluid flow divider may comprise one or more inflatable chambers or one or more deployable shrouds comprising a plurality of arms with a webbing extending between adjacent arms. The inflatable chambers may be relatively noncompliant or they may be compliant, exhibiting elastic behavior after initial inflation, to closely fit the aortic lumen size and curvature. The catheter may further include one or more additional or auxiliary flow control members located upstream or downstream from the fluid flow divider to further segment the patient's circulatory system for selective perfusion to different organ systems within the body or to assist in anchoring the catheter in a desired position.

25 Claims, 17 Drawing Sheets

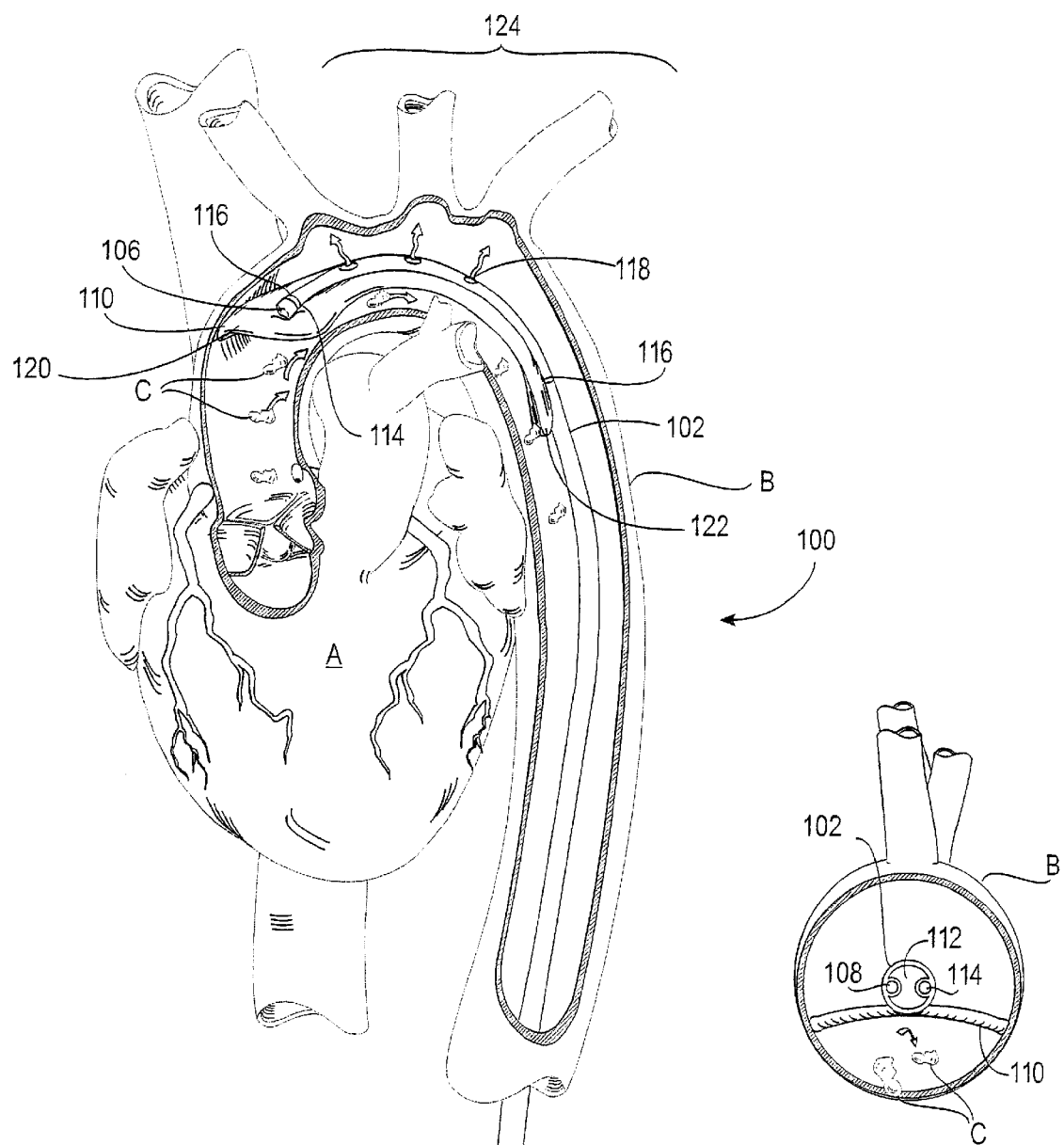
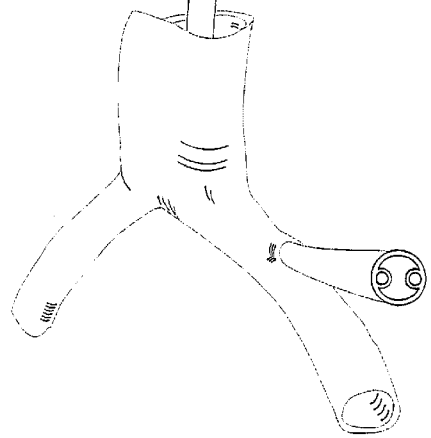
FIG 5
FIG 7

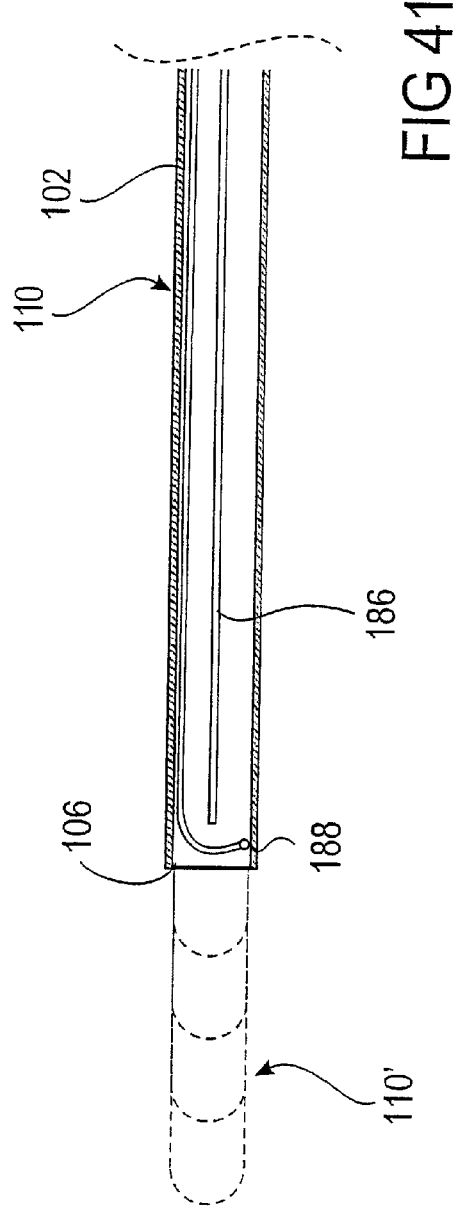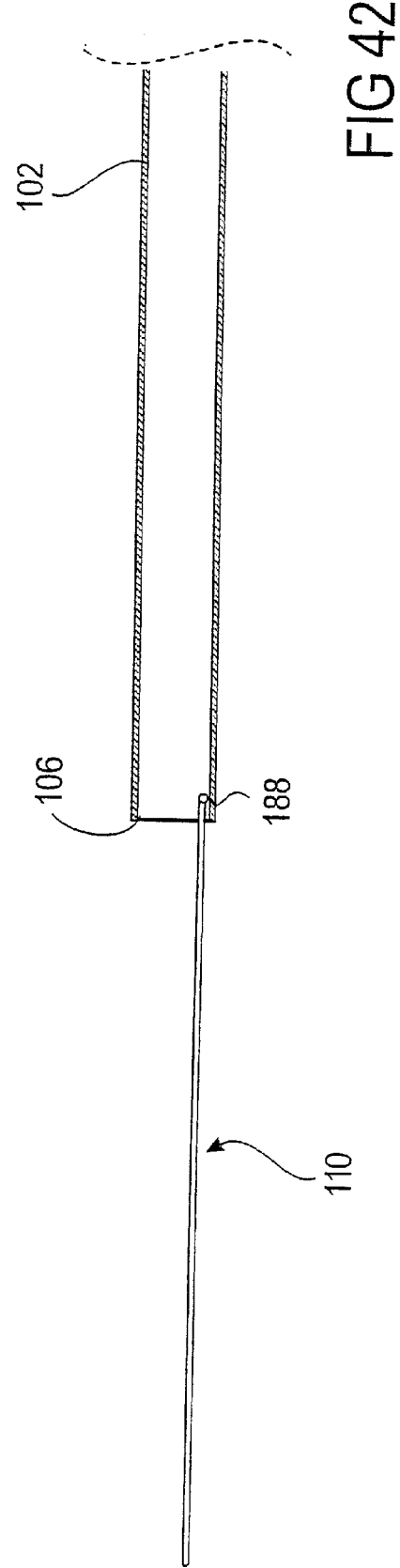

METHODS OF MAINTAINING SELECTIVE FLOW WITHIN A VESSEL

CROSS REFERENCE TO OTHER PATENT APPLICATIONS

This patent application is a continuation of U.S. patent application Ser. No. 09/378,676 filed Aug. 20, 1999 claiming the benefit of U.S. provisional patent application Ser. No. 60/116,836 filed Jan. 22, 1999.

FIELD OF THE INVENTION

This invention relates to a catheter system that reduces the volume of embolic material, which may be knocked loose from an artery wall or the wall of a chamber of the heart as a result of a medical procedure, from entering a selected oxygenated blood carrying artery system. More specifically, the invention relates to a catheter for isolating and perfusing a segment of a patient's cardiovascular system and for directing circulatory flow around the isolated segment. More particularly, it relates to an apparatus for deployment within a patient's aortic arch and to methods for selectively perfusing the arch vessels with a fluid, while directing blood flow within the aortic lumen past the isolated arch vessels.

BACKGROUND OF THE INVENTION

In the field of cardiovascular surgery, it has been common practice for surgeons to perform a sternotomy to expose the body cavity in the thorax region, wherein retractors are employed to provide the necessary access to internal structures to perform the necessary medical procedures. Depending on the medical procedure to be performed, it has often been necessary to arrest heart activity for some period of time during the procedure. The blood is then diverted through a cardiopulmonary bypass pump in order to maintain sufficient oxygenated blood flow to the body. Procedures performed as described above cause significant trauma to the body due to the method of entry into the thorax region, and the cessation of heart activity. Recent trends in the development of surgical devices have been toward the use of less invasive techniques, so that operations cause less extensive trauma. Furthermore, there has been a trend toward reducing the amount of time the heart is stopped, or eliminating the step of stopping the heart.

One major disadvantage to any procedure performed on the heart or on major arteries associated with the heart, even for less invasive procedures, is that embolic material may be knocked loose from arterial walls, heart valves, or from the interior walls of the chambers of the heart, and pumped to the brain, where the resulting blockages may cause neurological damage.

Cardiopulmonary bypass pumps are frequently used to pump blood in the patient while the heart is stopped during surgery, and bypass pumps generally include a filter mechanism to trap embolic material from the blood before the oxygenated blood is returned to the body. However, when the heart is started embolic material from within the heart may be pumped to the brain. Aortic perfusion shunts, as described in commonly owned and copending U.S. patent application, Ser. No. 09/212,580, filed Dec. 15, 1998, claiming the benefit of provisional application, Ser. No. 60/069,470, filed Dec. 15, 1997, hereby incorporated in its entirety, have been developed that allow the blood from the heart to perfuse the body, while providing separate perfusion of the arch vessels. The aortic perfusion shunts described represent a significant step forward in protection against cerebral embolization, however, there remains a tremendous need for further improvements in devices and methods for protecting a patient against the potential of cerebral embolization.

What is needed is a catheter device for use in minimally invasive medical procedures and for standard open chest surgery that is simple and relatively inexpensive and that is capable of isolating the circulation of the arch vessels, while still allowing the heart to perform the function of perfusing the body of the patient.

SUMMARY OF THE INVENTION

Accordingly, the invention is a catheter with a fluid flow control member called a deflector or a fluid flow divider positioned near the distal end of the catheter for dividing a first lumen into two channels near a point where a second lumen branches from the first lumen, and for perfusing the branch lumen. The invention will be described more specifically herein relating to an aortic catheter having a divider positioned in the aortic arch proximate the arch vessels.

The flow divider may be formed in a variety of configurations. In general the flow divider will have an undeployed or collapsed state and an expanded or deployed state. The flow divider may be deployed from an exterior surface of the catheter shaft, or it may be deployed from within a lumen in the catheter shaft. In embodiments wherein the flow divider is coupled to an exterior surface, the flow divider will preferably have an undeployed state wherein the flow divider is contained in a relatively small volume around the circumference of the distal end (nearest the heart) of the catheter, having an exterior circumference that is preferably not significantly larger than the exterior circumference of the catheter. In embodiments wherein the flow divider is deployed from within the catheter, the flow divider preferably has an undeployed state that is sized and configured for storage within a lumen in the catheter. In both configurations, the catheter will generally have a deployed state in which the length and width of the flow divider is sufficient to divide blood flow in the aorta in the vicinity of the ostia of the arch vessels.

The flow divider may comprise one or more inflatable chambers or one or more selectively deployable shrouds. The inflatable chambers may be relatively non-compliant or they may be compliant, exhibiting elastic behavior after initial inflation to closely fit the aortic lumen size and curvature.

The catheter may further include one or more additional or auxiliary flow control members located upstream or downstream from the flow divider to further segment the patient's circulatory system for selective perfusion to different organ systems within the body or to assist in anchoring the catheter in a desired position. These auxiliary flow control members may comprise inflatable balloons or selectively deployable external catheter valves. The anchoring members may be inflatable balloons or other anchoring structures that provide sufficient force or friction to prevent the catheter from drifting from a selected position within the aorta.

In a preferred embodiment, the catheter shaft includes at least three lumens, one lumen for inflating or otherwise deploying the flow divider, a second for perfusion of the arch vessels, and a third guidewire lumen. In alternate embodiments, additional lumens may be included for deploying the auxiliary flow control members, and for measuring the pressure at desired locations within the aorta. The catheter may be configured for retrograde deployment via a peripheral artery, such as the femoral artery, or it may be configured for antegrade deployment via an aortotomy incision or direct puncture in the ascending aorta.

Methods according to the present invention are described using the aortic catheter for occluding and compartmentalizing or partitioning the patient's aortic lumen and for performing selective filtered aortic perfusion.

BRIEF DESCRIPTION OF THE DRAWINGS

FIG. 5 shows a perspective view of the distal region of the catheter of FIG. 1 deployed within an aortic arch.

FIG. 6 shows a side view of the catheter of FIG. 5 deployed within an aortic arch.

FIG. 7 shows a lateral cross section of the aortic lumen and of the catheter of FIG. 6 taken along line 7—7.

FIG. 41 shows an embodiment of the flow divider comprising a flexible tongue that is folded back within the catheter shaft, and deployed using a deployment wire to push the flow divider out.

FIG. 42 shows the flow divider of FIG. 41 fully deployed, and with the deployment wire retracted.

DETAILED DESCRIPTION OF THE INVENTION

Figure 1:
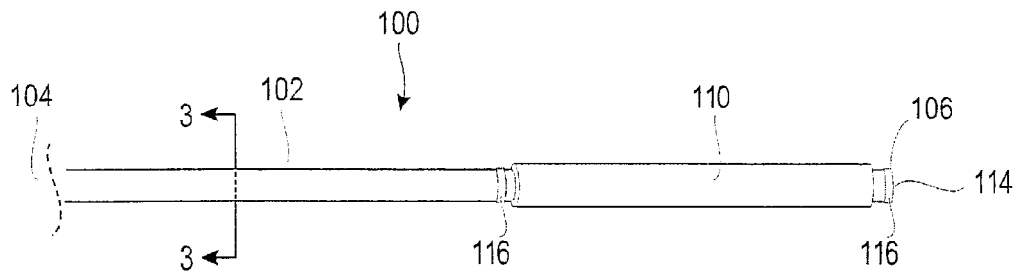
FIG. 1 shows a bottom view of a first embodiment of the aortic catheter of the invention configured for retrograde deployment via a peripheral artery access point, such as the femoral artery.

The catheter described herein with all of its preferred features represents a versatile device having multiple uses. The invention provides a catheter having a flow divider, indicated generally by the reference number 110 in the accompanying drawings, positioned near the distal end of the catheter for dividing the blood flow through a lumen, preferably at a point where at least one second lumen branches from the first lumen, and for perfusing the branch lumen or lumens. However, the invention will be described more specifically herein relating to an aortic catheter having a flow divider 110 configured to be positioned in the aortic arch and having a length sufficient to divide the blood flow in the aortic lumen so that the arch vessels are at least partially isolated.

The flow divider 110 may be formed in a variety of configurations. In general the flow divider 110 will have an undeployed state wherein the flow divider 110 is contained in a relatively small volume around the circumference of the distal end of the catheter, nearest the heart. The catheter will generally have a deployed state in which the length and width of the flow divider 110 is sufficient to divide blood flow in the aorta in the vicinity of the ostia of the arch vessels, and an undeployed state in which the flow divider 110 is collapsed around the shaft of the catheter and preferably has an exterior circumference that is not significantly larger than the exterior circumference of the catheter.

The flow divider 110 may comprise one or more inflatable chambers or one or more selectively deployable shrouds. The balloons may be relatively non-compliant or they may be compliant, exhibiting elastic behavior after initial inflation, for example, to closely fit the aortic lumen size and curvature.

The catheter may further include one or more additional or auxiliary flow control members located on the catheter either distal or proximal from the flow divider 110 to further segment the patient's circulatory system for selective perfusion to different organ systems within the body or to assist in anchoring the catheter in a desired position. These auxiliary flow control members may comprise inflatable balloons or selectively deployable external catheter valves. The anchoring members may be inflatable balloons or other anchoring structures that provide sufficient force or friction to prevent the catheter from drifting from a selected position within the aorta.

Usable auxiliary flow control members include, but are not limited to, expandable or inflatable members such as inflatable balloons and valves including collapsible/expandable valves of various configurations including retrograde valves, antegrade valves, and various central flow and peripheral flow valves. A combination of valves and inflatable members may be used as appropriate for a given procedure, thus in some embodiments, the catheter body can include one or more antegrade and retrograde valves, as well as one or more inflatable balloons. Inflatable balloons and collapsible/deployable valves have been previously described, and are known in the industry, and any desirable or practical inflatable balloon or deployable valve may be used. Inflatable balloons typically include an interior chamber that is in fluid communication with an inflation lumen extending within the catheter shaft from a location from within the respective flow control member to a location in the proximal portion which is adapted to extend out of the patient.

Preferably, the flow divider 110, and any auxiliary flow control members, or anchoring members, if present, are mounted directly on an elongated catheter shaft. In a preferred embodiment, the catheter shaft includes at least three lumens, one lumen for inflating or otherwise deploying the flow divider 110, a second for perfusion of the arch vessels, and a third guidewire lumen. In alternate embodiments, additional lumens may be included for deploying the auxiliary flow control members, for measuring the pressure at desired locations within the aorta, or for perfusing other isolated segments of the patient's circulatory system. The catheter may be configured for retrograde deployment via a peripheral artery, such as the femoral artery, or it may be configured for antegrade deployment via an aortotomy incision or direct puncture in the ascending aorta. The catheter is characterized by a flexible catheter shaft placed by surgical cutdown or needle/introducer guidewire technique into the vessels of the lower or upper extremity or neck. Other large internal vessels may also be used.

Anticoagulants, such as heparin and heparinoids, may be applied to the surfaces of the catheter and/or flow control members as desired. Anticoagulants may be painted or sprayed onto the device. Anticoagulants other than heparinoids may also be used, for example monoclonal antibodies such as REOPRO (Eli Lilly and Co., Indianapolis, Ind.). A chemical dip comprising the anticoagulant may also be used. Other methods known in the art for applying chemicals to catheters may be used.

Attention is now drawn to the figures, which illustrate examples of several embodiments of the invention, and wherein like numbers refer to similar elements or features. FIG. 1 illustrates a first embodiment of the aortic catheter 100 of the invention. The aortic catheter 100 has an elongated catheter shaft 102 having a proximal end 104, that preferably extends out of the patient's body, and a distal end 106 closest to the patient's heart. The elongated catheter shaft 102 preferably has an overall length sufficient to reach from the arterial access point where it is inserted into the patient to its deployed position within the aorta. For femoral artery deployment in adult human patients, the elongated catheter shaft 102 preferably has an overall length from approximately 60 cm to 120 cm, and more preferably 70 cm to 90 cm.

In a preferred embodiment, the elongated catheter shaft 102 has an outer diameter that is preferably approximately 9 to 22 French (3.0 to 7.3 mm), and more preferably 12 to 18 French (4.0 to 6.0 mm) for use in adult human patients. Catheters for pediatric use, or use in non-human subjects, may require different dimensions and would be scaled accordingly. The elongated catheter shaft 102 is preferably formed of a flexible thermoplastic material, a thermoplastic elastomer, or a thermoset elastomer. Suitable materials for use in the elongated catheter shaft 102 include, but are not limited to, polyvinylchloride, polyurethane, polyethylene, polyamides, polyesters, silicone, latex, and alloys or copolymers thereof, as well as braided, coiled or counterwound wire or filament reinforced composites. Additionally or alternatively, the elongated catheter shaft 102 may be constructed using metallic tubing or a solid wire, for example stainless steel hypodermic tubing or wire or superelastic nickel-titanium alloy tubing or wire. Preferably, the aortic catheter 100 includes one or more location markers 116, such as radiopaque markers and/or sonoreflective markers, to enhance imaging of the aortic catheter 100 during deployment using standard fluoroscopy, ultrasound, MRI, MRA, transesophageal echocardiography, or other techniques. For example, in the illustrative embodiment shown in FIG. 1, a radiopaque location marker 116 is positioned near the distal end 106 of the catheter shaft 102, and another near the proximal end of the flow divider 110, to assist in positioning the flow divider 110 within the aortic arch. The radiopaque location markers 116 may be formed as a ring or disk of dense radiopaque metal such as gold, platinum, tantalum, tungsten, or compounds or alloys thereof, or a ring of a polymer or adhesive material heavily loaded with a radiopaque filler material.

Figure 2:
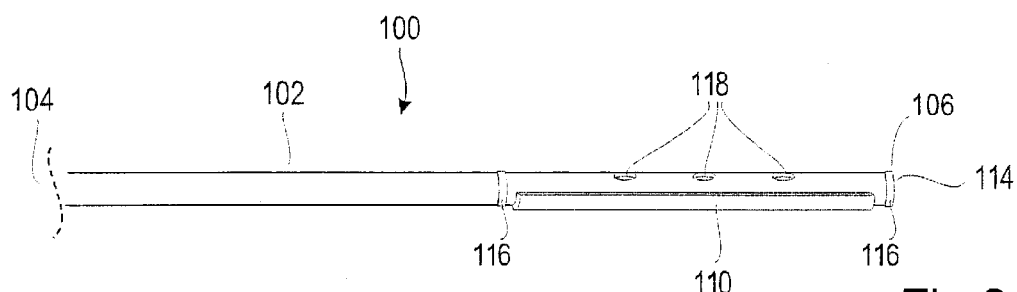
FIG. 2 shows a side view of the catheter of FIG. 1, showing the divider in a collapsed state.

The flow divider 110, of FIG. 1, is mounted proximate the distal end 106 of the elongated catheter shaft 102. In the embodiment shown in FIGS. 1 through 4, the flow divider 110 is shown in the form of a flat elongate expandable inflatable balloon bonded to the catheter shaft 102 by heat welding or with an adhesive. The inflatable flow divider 110 has a deflated state in which the flow divider 110 adheres closely to the catheter shaft 102 so that the collapsed diameter of the flow divider 110 is, preferably, not substantially larger than the diameter of the catheter shaft 102, and an inflated state in which the flow divider 110 expands to dimensions sufficient to divide blood flow in the aortic arch of the patient into two fluid flow channels. Preferably, the flow divider 110 will be formed so that, when inflated, the flow divider 110 automatically assumes and maintains a desired shape, without any additional stiffening structure. However, in some embodiments, it may be desirable to include means for assisting the flow divider 110 in maintaining a desired shape, and any known means for accomplishing this may be used. For example, the divider may include ribs or other stiffening structures coupled to the flow divider 110, or formed as an integral part of the flow divider 110. Alternatively, the flow divider 110 may include mattress type welds, or internal welds or columns. The outer surface of flow divider 110 may include a friction increasing means such as a friction increasing coating or texture to increase friction between the flow divider 110 and the aortic wall, when deployed, to assist in maintaining the flow divider 110 in a desired position within the aorta. FIG. 2 is a side view of the catheter 100, showing that the flow divider 110 is preferably coupled only to a portion of the diameter of the catheter shaft 102. Thus, perfusion ports 118 are unobstructed.

Figure 3:
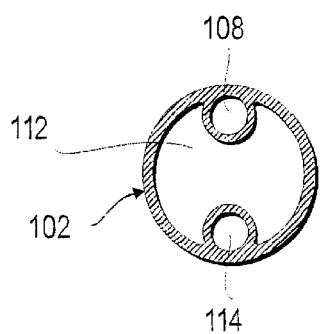
FIG. 3 shows a cross section of the aortic catheter of FIG. 1 taken along line 3—3 in FIG. 1.

FIG. 3 is a cross section of the catheter shaft 102 taken along line 3—3. The elongated catheter shaft 102 preferably has at least three lumens, an inflation lumen 108 that is used to deploy the flow divider 110, a perfusion lumen 112 that is used to perfuse one of the fluid flow channels, and a guidewire lumen 114. The configuration of the lumens is shown for illustrative purposes only, and any reasonable configuration of lumens within the catheter may be used.

Figure 4:
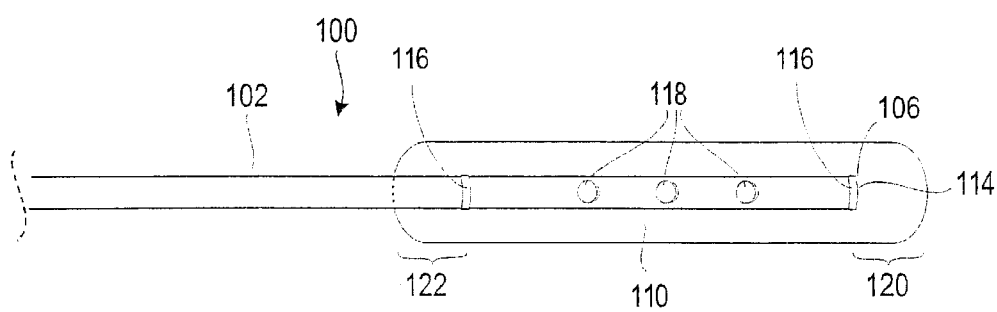
FIG. 4 shows a top view of the catheter of FIG. 1 with the flow divider deployed.

The flow divider 110 is shown in a deployed state in FIG. 4. Preferably, the flow divider 110 in its deployed configuration includes a distal portion 120 that extends beyond the distal end of the catheter 100 in order to seal snugly against the aortic lumen wall. The proximal portion 122 of the divider 110 is shown shaped similarly to the distal portion 120, however, in this embodiment the shape of the proximal portion 122 of the divider 110 is not critical to the invention and could be triangular, square, or any other desired shape. In other embodiments, it may be preferable that the shape be chosen to encourage low turbulence, or possibly laminar, fluid flow where the fluid flow from the flow channel above the divider 110 and the fluid flow from below the flow divider 110 meet at the trailing edge of the proximal portion 122.

Referring to FIG. 5, an aortic catheter 100 of the invention is shown in a cutaway perspective view deployed within a patient's aorta B via femoral artery access. In order to facilitate placement of the catheter 100 within the aorta B, and to improve the stability of the catheter 100 in the proper position in the patient's aorta B, a distal region 124 of the aortic catheter 100 may be preshaped to conform to the internal curvature of the patient's aortic arch. The distal region 124 represents a J-shaped curve of approximately 180 degrees of arc with a radius of curvature of approximately 4 to 10 centimeters, for use in a typical adult human patient.

The distal end 106 of the aortic catheter 100 may be skewed slightly out of the plane to accommodate the forward angulation of the typical patient's aortic arch and ascending aorta.

In use, the flow divider 110 is positioned within the aortic arch, as seen in a side view in FIG. 6, with the flow divider 110 positioned to redirect blood flow originating from the heart A through a selected region of the aortic lumen B below the divider 110. The edge of the distal end 120 of the flow divider 110, as well as the sides of the flow divider 110, contact the aortic wall. Thus, the aortic lumen B is divided into two channels, one above the aortic divider 110 and one below the aortic divider 110. Blood flow originating from the heart A is prevented from entering the region of the aortic lumen providing blood flow to the arch vessels by the flow divider 110, which directs the blood to the flow channel below the flow divider 110. Blood flow below the flow divider 110 bypasses the arch vessels carrying any embolic material C harmlessly past the cerebral circulatory system. The channel above the flow divider 110 is perfused with a selected fluid, such as oxygenated normothermic blood, oxygenated hypothermic blood, blood substitutes such as PERFLUBRON or other perfluorocarbon compounds, radiopaque dyes for angiography, or the like, introduced through the perfusion lumen 112 of the catheter shaft 102. The selected fluid exits the catheter shaft 102 through perfusion ports 118. Because the proximal end 122 of the flow divider 110 is not sealed against a wall of the aortic lumen B, it is preferable that the pressure and flow rate of fluid perfused through the catheter 100 be sufficient to prevent back flow from the proximal end 122 of the divider 110 and also to hinder fluid flow around the edges of the flow divider 110. Thus, preferably, only the perfused fluid from the perfusion lumen 112 enters the arch vessels.

In the embodiment shown in FIGS. 1 through 7, it is contemplated that some of the selected fluid perfused through the perfusion ports 118 will flow to the arch vessels, and some will flow along the upper surface of the flow divider 110 until the perfused fluid leaves the trailing edge of the flow divider 110. It may be preferable that the blood flow at this point be laminar with little mixing between the fluid originating from the flow channels. However, even if turbulence results near the trailing edge of the flow divider 110, embolic material C in the blood originating from the heart A will have already passed the arch vessels, thereby achieving the objective of preventing embolic material from entering the cerebral circulatory system.

It is not essential that the edges of the flow divider 110 create a perfect seal with the wall of the aorta. Some leakage of blood around the flow divider 110 may be tolerated because the fluid perfused through the perfusion lumen 112 creates a pressure gradient from above the flow divider 110 to below the flow divider 110 so that any potential embolic material will not enter the flow channel above the flow divider 110.

Figure 8:
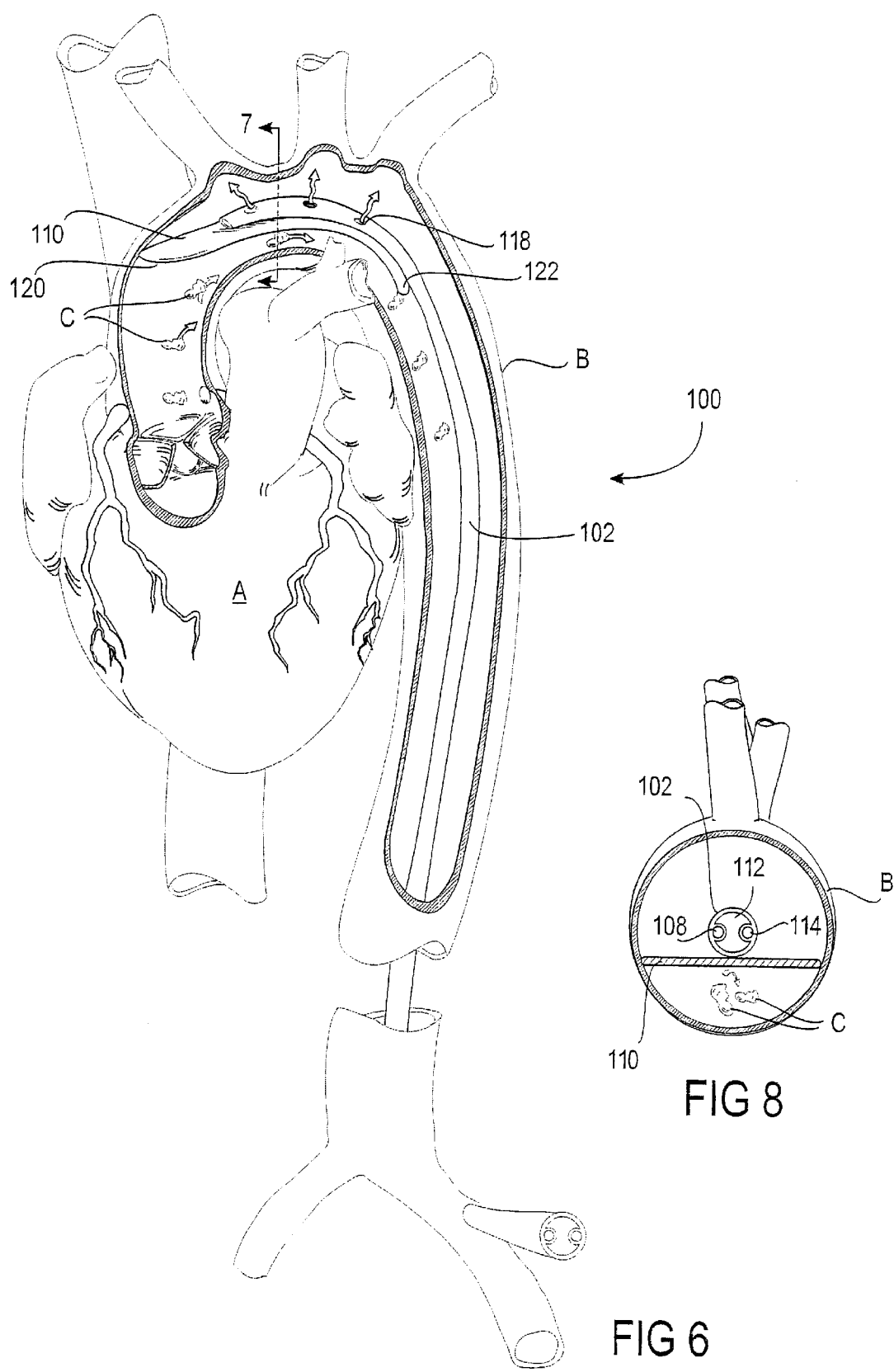
FIG. 8 shows an alternate embodiment of the catheter of FIG. 7, with the flow divider curved in a direction opposite that shown in FIG. 7.

The ability to create a good seal between the aortic lumen and the edges of the flow divider 110 may be enhanced by pre-shaping the flow divider 110 to conform to the aortic lumen. The flow divider 110 may be arcuate along the longitudinal axis of the flow divider 110 as is seen in FIG. 7, which shows a cross sectional view of the flow divider 110 taken along lines 7—7 in FIG. 6. The curve of the flow divider 110 may help prevent the flow divider 110 from collapsing against the aortic lumen wall when the upper side of the divider 110 is under greater pressure than the lower side of the flow divider 110. As shown in FIG. 8, in alternate embodiments, the arch of the flow divider 110 could be reversed.

Figure 9:
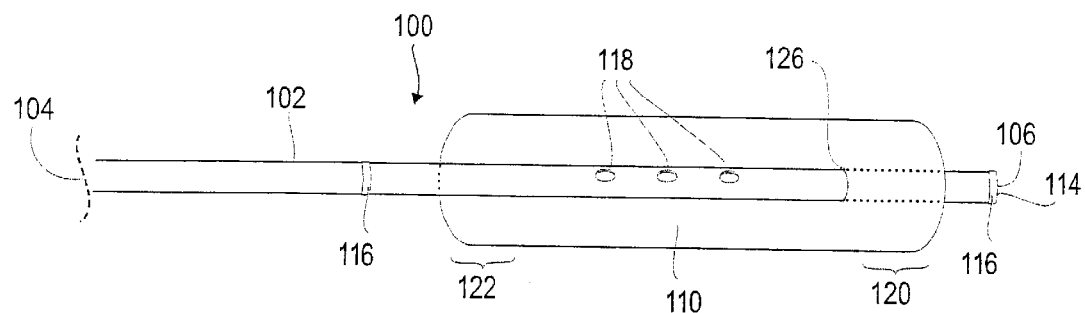
FIG. 9 shows an embodiment of the catheter of the invention wherein a distal end of the catheter extends through the divider and beyond the end of the divider.

In an alternate embodiment seen in FIG. 9, the distal end 106 of the catheter 100 passes through the flow divider 110 at a point 126 to extend on the opposite side of the flow divider 110. This configuration is useful for procedures wherein it is desired to perfuse the flow channel below the divider 110 with a selected fluid. The catheter 100 may use an additional separate corporeal perfusion lumen, or alternatively, the guidewire lumen 114 may be used. This embodiment is also usable for configurations including an auxiliary flow control member on the catheter positioned between the distal end 106 of the catheter 100 and the proximal end 122 of the flow divider 110.

Figure 10:
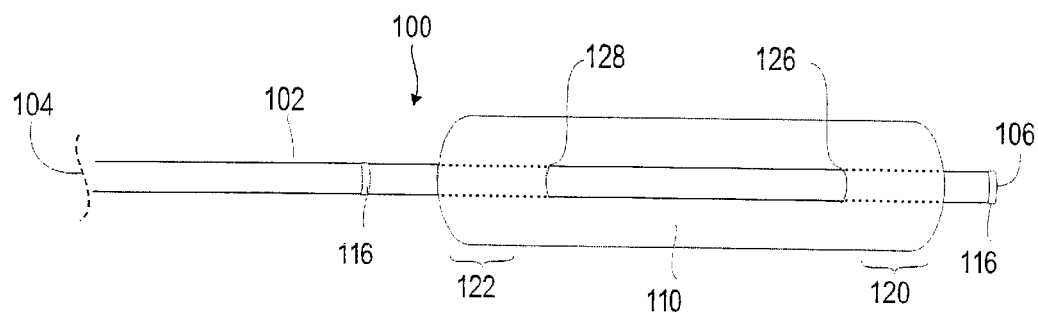
FIG. 10 shows an embodiment of the catheter of the invention wherein the catheter shaft extends below the divider, then above the divider, and then below the divider again, at different points along the catheter.
Figure 11:
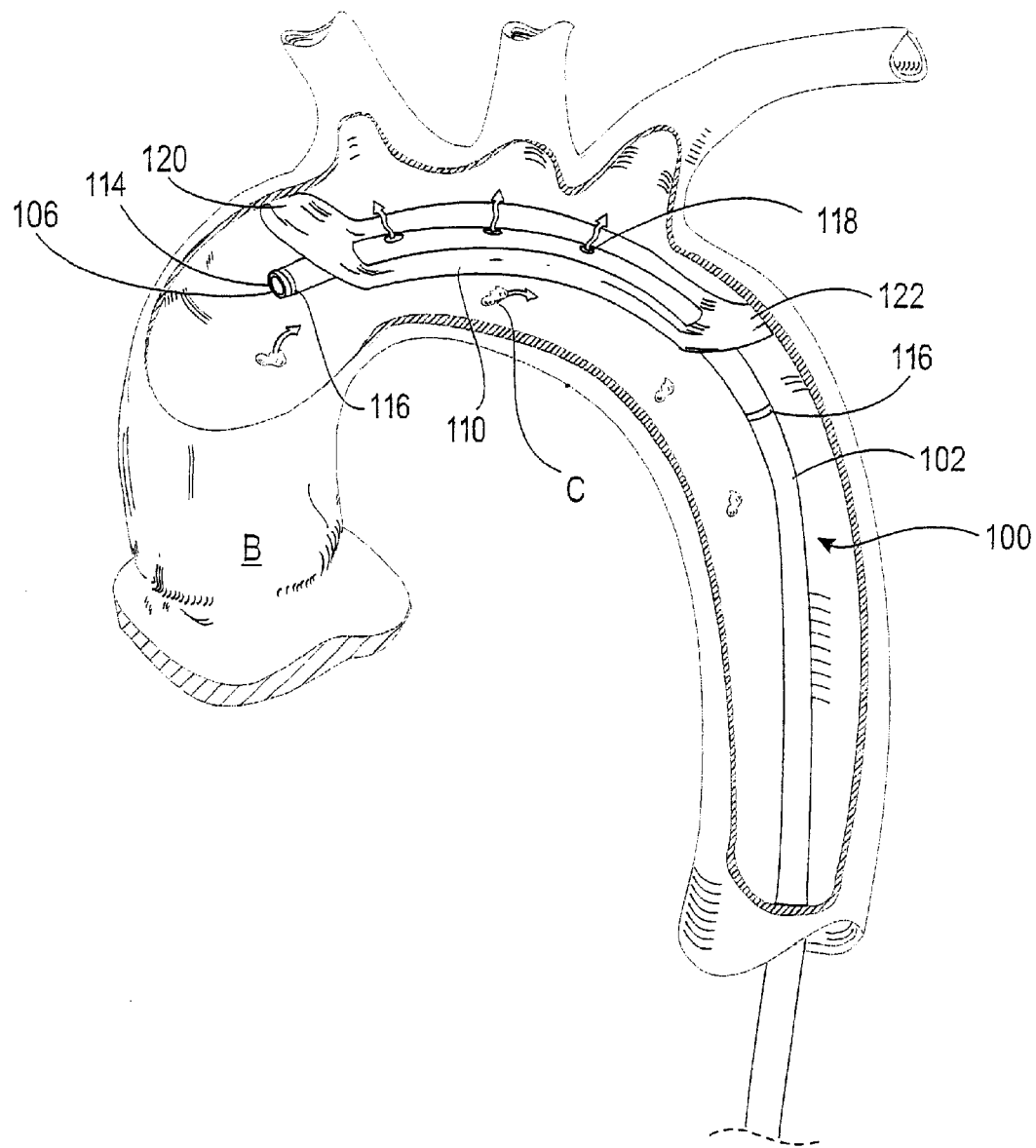
FIG. 11 shows a side view of the catheter of FIG. 10 deployed within the aortic arch.
Figure 12:
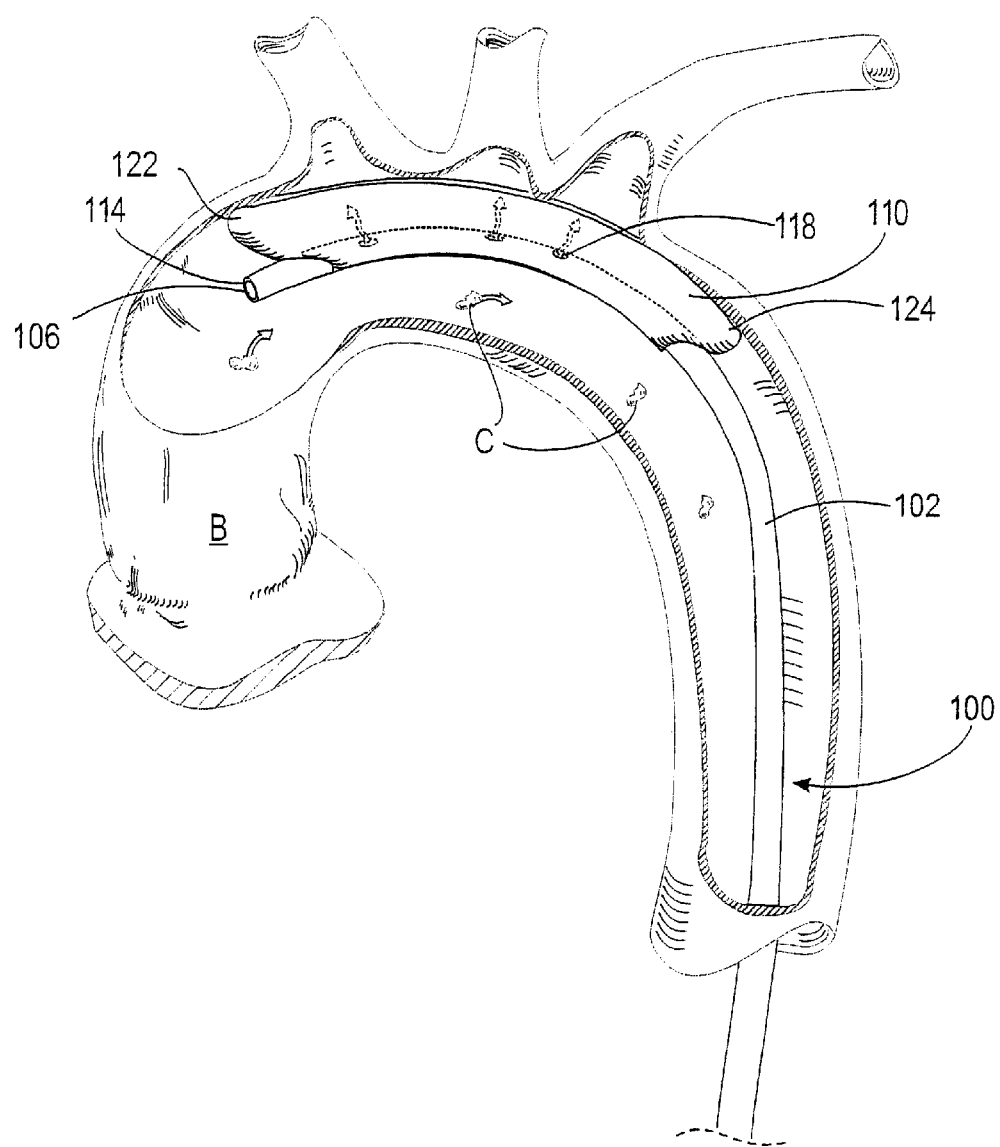
FIG. 12 shows a catheter similar to the catheter of FIG. 10, but with the divider periphery concave on its upper surface.

FIG. 10 discloses a catheter configuration wherein the catheter 116 passes from the lower side of the flow divider 110 at 128 to the upper side of the flow divider 110, and then, from the upper side of the flow divider 110 to the lower side of the flow divider at 126. The flow divider 110 is preferably arcuate, but in an orientation opposite that of the prior embodiments, as seen in the cut-away view of FIG. 8. Although, in alternate embodiments, the arch of the flow divider 110 could be reversed, as shown in FIG. 7. The catheter of this embodiment is seen in use in an aortic arch in FIG. 11. The advantage of this configuration is that both ends 120, 122 of the flow divider 110 seal against the aortic lumen wall, instead of the proximal end 122 of the flow divider 110 being open as in the previous embodiments. Furthermore, in this embodiment it may be preferable to maintain a higher pressure on the lower side of the flow divider 110 than on the upper side of the flow divider 110, for example by perfusing oxygenated blood through the guidewire lumen 114 or an additional separate corporeal perfusion lumen. If the pressure on the lower side of the flow divider 110 is maintained at a higher pressure than the pressure on the upper side of the flow divider 110, the flow divider 110 may be urged upward, causing the edges of the flow divider 110 to contact the aortic wall with greater force, assisting to seal the edges of the flow divider 110 against leakage. FIG. 12 shows a flow divider 110 similar to the flow divider 110 of FIG. 10, but with the flow divider 110 periphery concave upward, which may assist in sealing the edges of the flow divider 110 against leakage. However, a complete seal is not critical in these or any other embodiments of the invention described herein, as pressure gradients and/or balanced perfusion flow minimizes flow around the edges of the flow divider 110.

Figure 13:
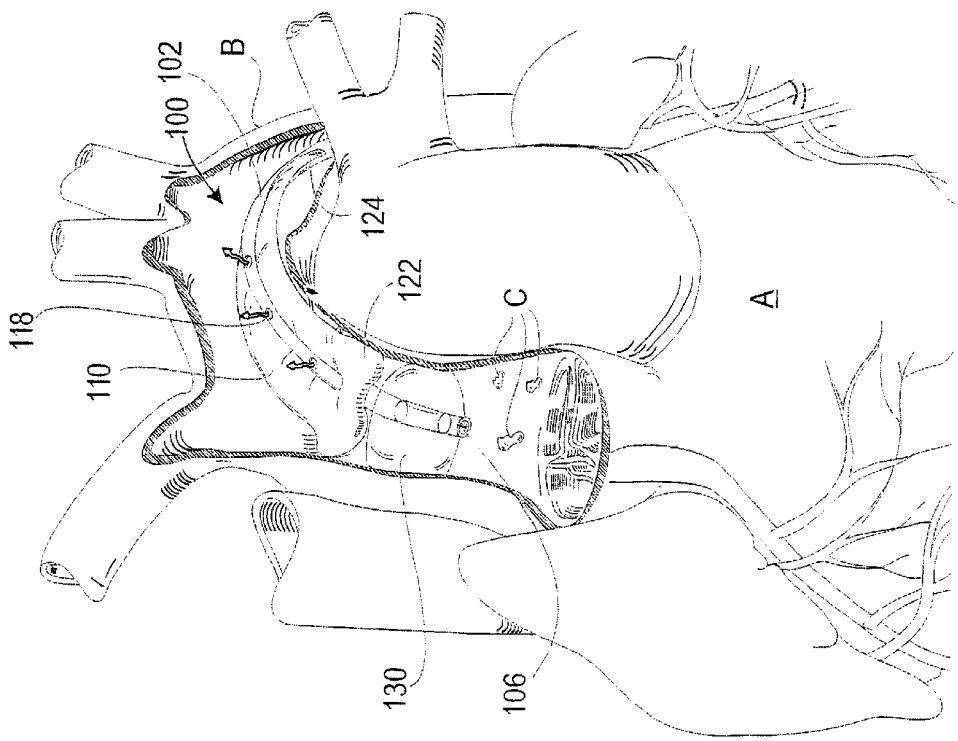
FIG. 13 shows a perspective view of an embodiment of the catheter of the invention including a deployed auxiliary flow control member positioned between the flow divider and the distal end of the catheter.

Any embodiments of the catheter 100 of the invention described above may further include auxiliary flow control members. The auxiliary flow control members may be used to further compartmentalize the patient's circulatory system, or may be used for other functions such as assisting in securely anchoring the catheter in a chosen position. An example of a catheter of the invention further comprising an auxiliary flow control member is seen in FIG. 13, which shows an auxiliary flow control member 130 coupled to the distal end of the catheter 100 proximate the distal end 122 of the flow divider 110. The auxiliary flow control member 130 is positioned within the aorta and is fully deployed, occluding the aorta. The auxiliary flow control member 130 shown in FIG. 13 is an inflatable balloon bonded to the catheter shaft 102 by heat welding or with an adhesive. Alternatively, the auxiliary flow control member 130 could be a deployable valve, or other structure. Deployable valves suitable for use in this application are described in commonly owned U.S. Pat. Nos. 5,827,237 and 5,833,671, which are hereby incorporated in their entirety. Suitable materials for the inflatable anchor member 130 include, but are not limited to, elastomers, thermoplastic elastomers, polyvinylchloride, polyurethane, polyethylene, polyamides, polyesters, silicone, latex, and alloys or copolymers and reinforced composites thereof. In alternate embodiments, the auxiliary flow control member 130 may be positioned on the proximal side of the flow divider 110, if desired. The auxiliary flow control member 130 may also be used to anchor the catheter 100 so that it does not migrate out of its optimal position during the medical procedure. The outer surface of an auxiliary flow control member 130 used to anchor the catheter 100 may include a friction increasing means such as a friction increasing coating or texture to increase friction between the auxiliary flow control member 130 and the aortic wall, when deployed. Alternatively, an auxiliary flow control member 130, which may be an inflatable balloon or deployable valve, can be mounted on a separate catheter and introduced through a lumen within the catheter 100.

Figure 14:
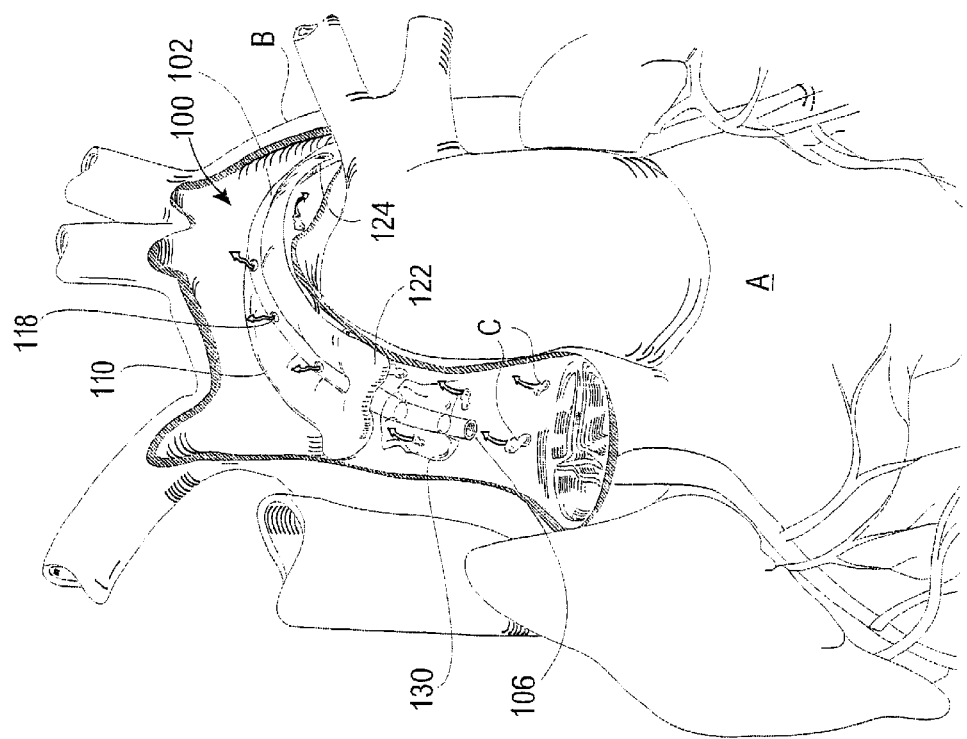
FIG. 14 shows a perspective view of the catheter of FIG. 13 with the auxiliary flow control member partially collapsed.

FIG. 14 shows the catheter of FIG. 13 deployed within an aorta with the flow divider 110 fully deployed, and auxiliary flow control member 130 partially collapsed. As blood flow resumes from the heart A, embolic material C is diverted away from the arch vessels by the flow divider 110.

Figure 15:
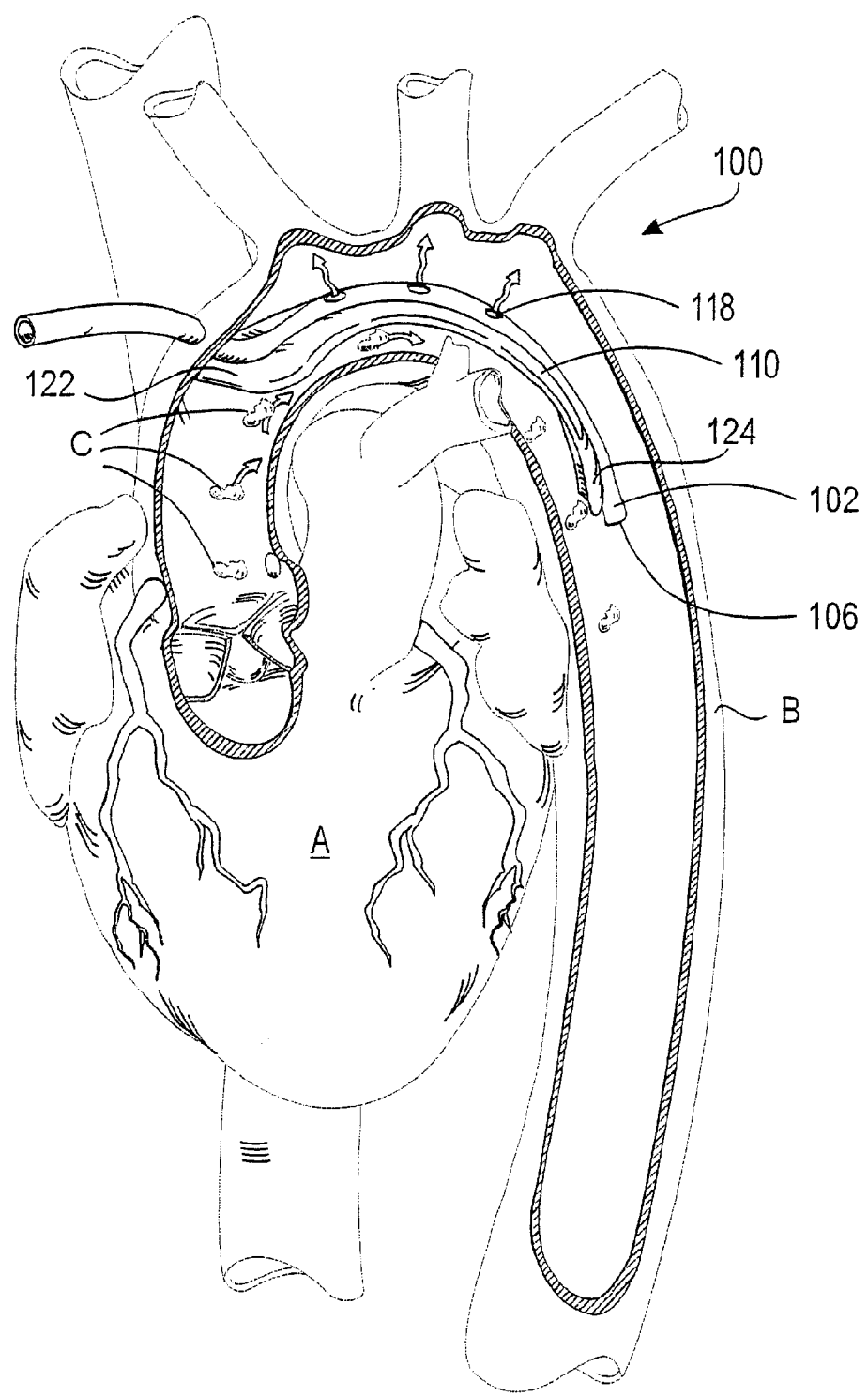
FIG. 15 shows an embodiment of the catheter of the invention configured for antegrade deployment.

The previous embodiments have been described using a catheter configured for a retrograde approach to the aorta from a peripheral vessel such as the femoral artery. The invention could easily be modified for alternate deployment means. For example, FIG. 15 shows a catheter 100 configured for central antegrade deployment in the aortic arch through an aortotomy or direct puncture in the ascending aorta. The catheter 100 and flow divider 110 is configured similarly to the catheters disclosed in previous embodiments. Other embodiments of the invention may be configured for peripheral insertion through the subclavian or axillary arteries.

Figure 16:
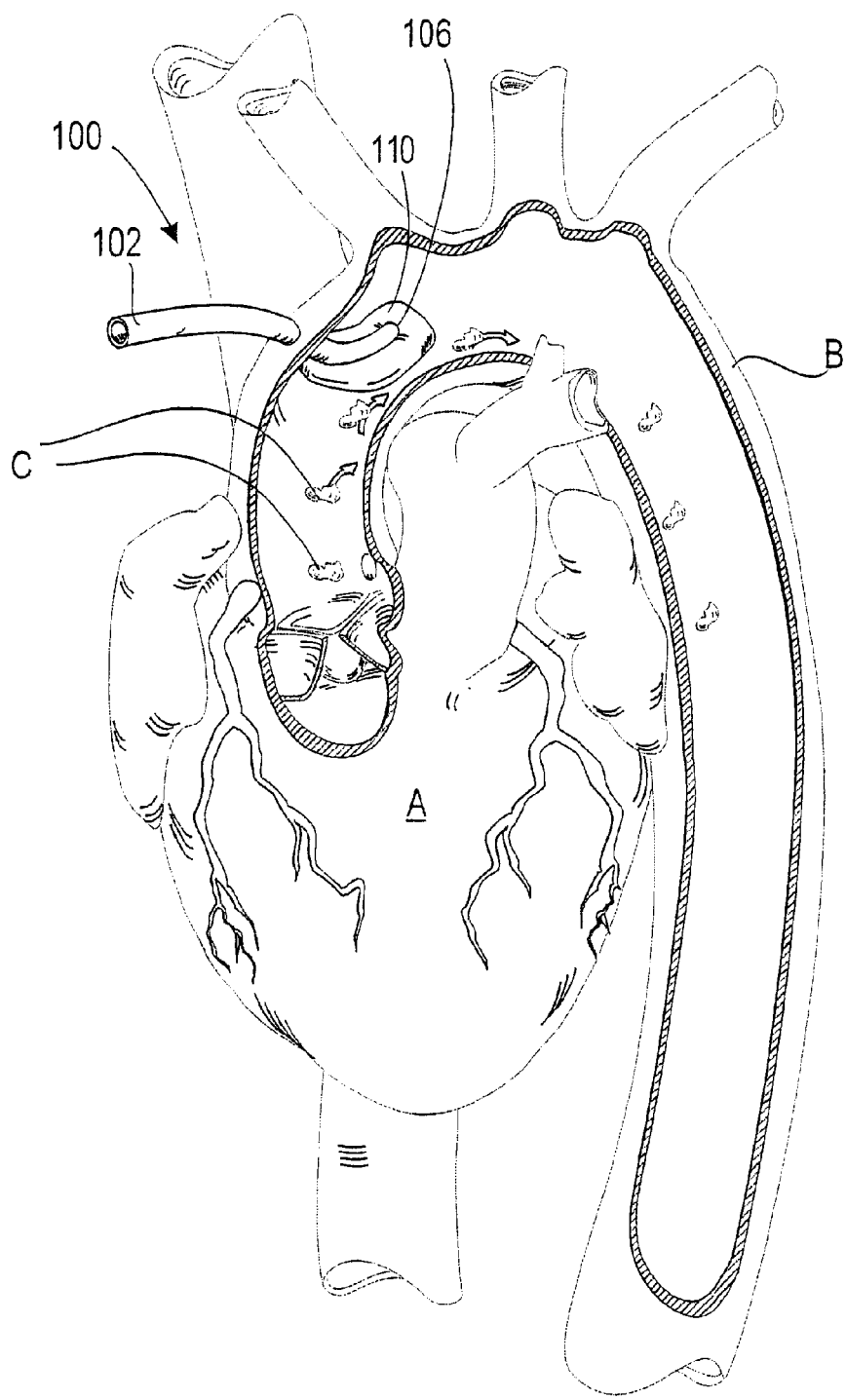
FIG. 16 shows another embodiment of the catheter of the invention configured for antegrade deployment, showing a divider that is significantly shorter than the divider described in previous embodiments.

FIG. 16 shows an alternate embodiment having a very short flow divider 110. In this embodiment, the flow divider 110 does not extend beyond the ostia of the arch vessels, and relies on the creation of two adjacent fluid flow streams or channels that preferably exhibit laminar flow, or low turbulence flow between the two flow streams. Even if some turbulence results near the trailing edge of the flow divider 110, embolic material C in the blood originating from the heart A will preferably have passed the arch vessels before the fluid streams mix significantly. Preferably, the arch vessels receive fluid only from the flow stream originating from the perfusion ports 118 above the flow divider 110.

Figure 17:
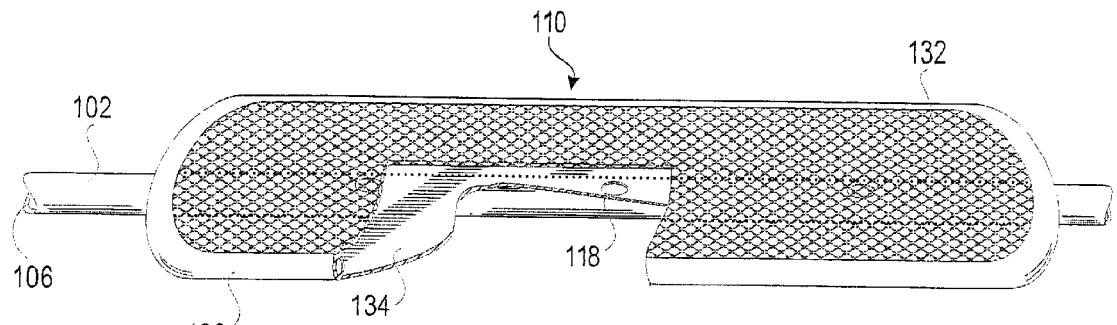
FIG. 17 shows a cut-away view of an embodiment of the flow divider including a mesh or porous portion for perfusing from the upper surface of the flow divider.
Figure 18:
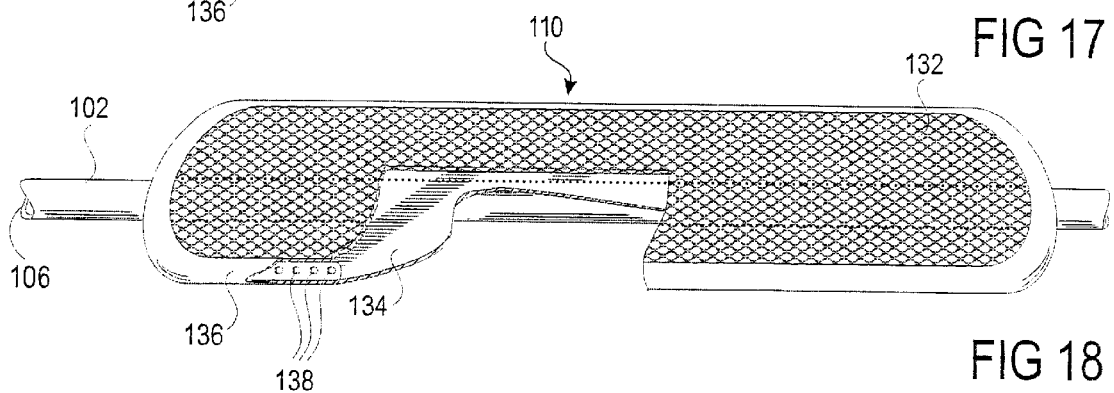
FIG. 18 shows a cut-away view of an alternate internal structure of the flow divider of FIG. 17.

FIG. 17 discloses an alternate embodiment of the flow divider 110, wherein the top surface of the flow divider 110 comprises a mesh or porous region 132. The perfusion ports 118 allow a selected fluid to enter the interior chamber 134 of the flow divider 110 before the fluid passes through the mesh or porous region 132 to perfuse the aorta. The material or materials used in the flow divider 110 are preferably characterized by properties that allow an internal pressure within the flow divider 110 to be maintained at a sufficient level to maintain the deployed configuration of the flow divider 110 to divide the aorta, while also allowing a controlled volume of fluid to escape from the flow divider 110 through the mesh or porous region 132 on the upper surface of the flow divider 110 for perfusing the arch vessels. Thus, the surface of the flow divider 110 may have porous regions that allow a fluid to be perfused at a known rate when a specific pressure is attained. In the embodiment shown in FIG. 17, an inflatable peripheral tube 136 surrounds the periphery of the flow divider 110, however, in alternate embodiments, this feature may be omitted. In embodiments including an inflatable peripheral tube 136, it is preferable that the peripheral tube 136 be inflated from a separate additional lumen. However, FIG. 18 discloses an embodiment of the flow divider 110 of FIG. 17 wherein a single inflation and perfusion lumen may be used. In this embodiment, perfused fluid passes from the catheter 100 into the peripheral tube 136 to inflate the peripheral tube 136. Apertures 138 between the inflatable peripheral tube 136 and the interior chamber 134 of the flow divider 110 allow fluid to flow from the peripheral tube 136 into the chamber 134 within the inflatable flow divider 110. The fluid then passes through the mesh or porous region 132 of the flow divider 110 to perfuse the aorta. Preferably, the apertures 138 of the peripheral tube 136 are sized so that the pressure within the peripheral tube 136 is higher than the pressure within the chamber 134 of the flow divider 110.

The porous and non-porous sections of the flow divider 110 may be formed from the same or separate materials. Suitable materials for the non-porous portions of the flow divider 110 include, but are not limited to, elastomers, thermoplastic elastomers, polyvinylchloride, polyurethane, polyethylene, polyamides, polyesters, silicone, latex, and alloys or copolymers, and reinforced composites thereof. Suitable materials for the porous portions of the flow divider 110 include meshes, woven and nonwoven fabrics, and porous membranes, such as microperforated or laser perforated polymer or elastomer films. For example, polyester meshes may be used, such as meshes made by Saati Corporations and Tetko, Inc. These are available in sheet form and can be easily cut and formed into a desired shape. Other meshes and porous materials known in the art, which have the desired characteristics, are also suitable.

Figure 19:
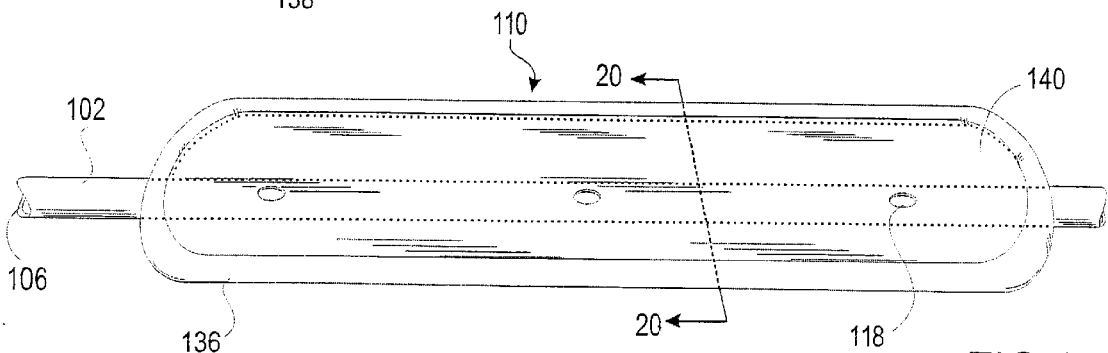
FIG. 19 shows an embodiment of the flow divider of the invention comprising a peripheral tube and membrane structure.
Figure 20:
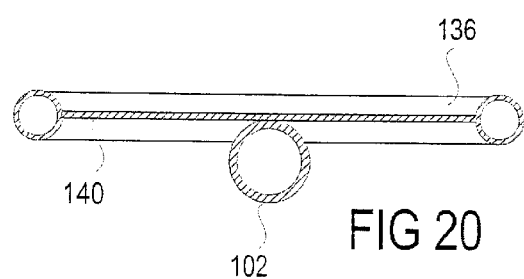
FIG. 20 shows a cross section of the flow divider of FIG. 19 taken along line 20—20.

Referring to FIG. 19, an embodiment of the flow divider 110 is disclosed having a nonporous film 140 surrounded by a peripheral tube 136 acting as a support structure. Inflation of the peripheral tube 136 causes deployment of the film 140 within the aorta. Holes are positioned over the perfusion apertures 118 to allow perfusion of the region above the flow divider 110. FIG. 20 is a cross section view of the flow divider 110 of FIG. 19 taken along line 20—20. It is possible to make the flow divider 110 of FIG. 19 by fabricating an oval balloon and affixing the central portion of the top and bottom layers together, leaving a peripheral region where the upper and lower layers are not coupled together forming the inflatable peripheral tube 136. Alternatively, the peripheral tube 136 and film 140 of the flow divider 110 may be formed of separate components and affixed together by a known means for joining such materials, such as by heat welding or adhesives.

Figure 21:
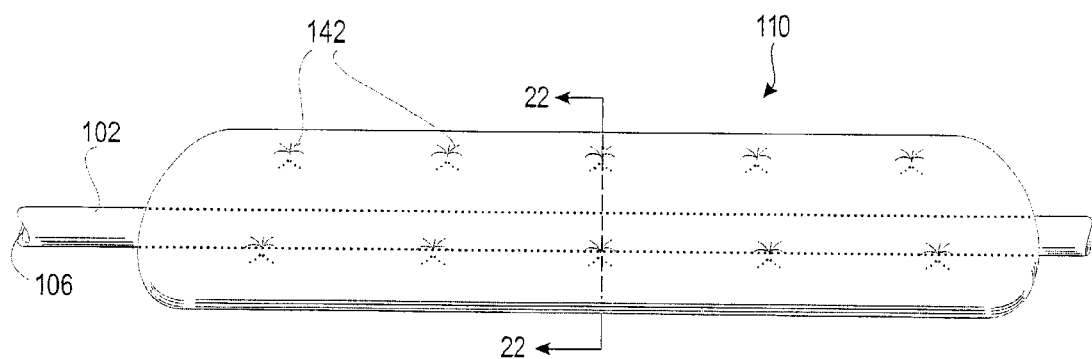
FIG. 21 shows an embodiment of the flow divider of the invention with welds or joined areas between an upper and a lower film of the flow divider to give additional structure and rigidity to the flow divider.
Figure 22:
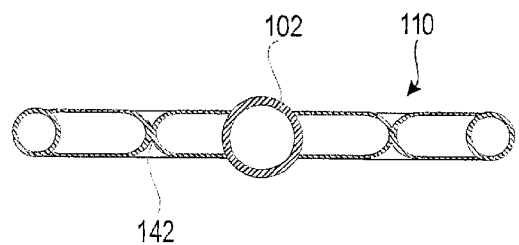
FIG. 22 shows a cross section of the flow divider of FIG. 20 taken along line 22—22.
Figure 23:
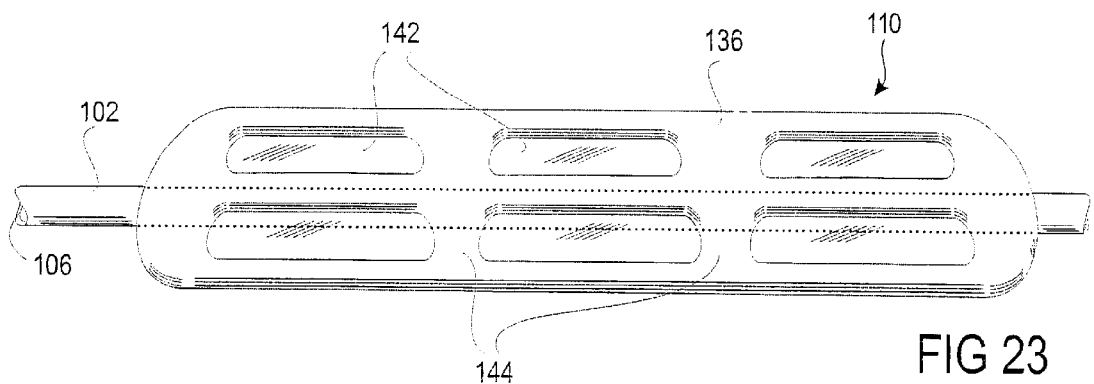
FIG. 23 shows an alternate embodiment of FIG. 21 with larger joined areas between the upper and lower films of the flow divider.

FIGS. 21–23 represent alternate embodiments of the flow divider 110 with welds or joined areas 142 between an upper and a lower film of the flow divider 110 to give additional structure and rigidity to the flow divider 110. FIG. 21 discloses an embodiment wherein the interior surface of the upper film has been coupled to the interior surface of the lower film, preferably by spot heat welding or adhesive. The resulting structure maintains the geometry of the flow divider 110 and provides it with additional rigidity. FIG. 22 is a cross section view of the flow divider 110 of FIG. 21 taken along line 22—22. FIG. 23 shows an alternate embodiment of FIG. 21 with larger joined areas 142 between the upper and lower films of the flow divider 110 creating well defined peripheral tube 136 and lateral or branch support members 144. In alternative embodiments, the film 140 and peripheral tube 136 and lateral or branch support members 144 may be fabricated as separate components and joined using any known means for doing so, including the use of adhesive or heat welding.

Figure 24:
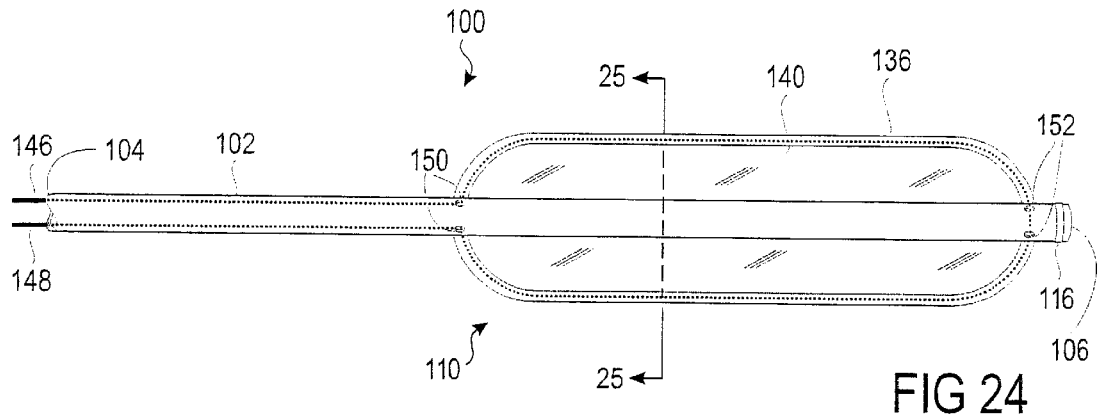
FIG. 24 shows an embodiment of the flow divider having a membrane or film portion and a peripheral tube portion, that is deployed using a pair of wires.
Figure 25:
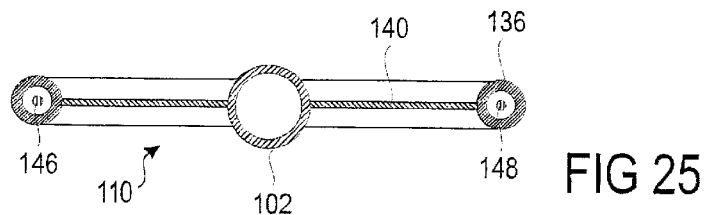
FIG. 25 shows a cross section of the flow divider of FIG. 24 taken along line 25—25.
Figure 26:
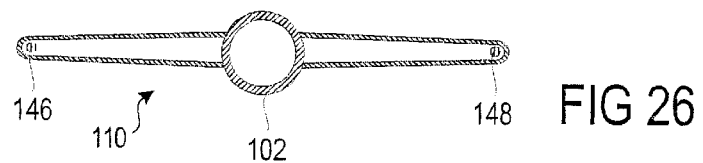
FIG. 26 shows a cross section of an embodiment of the flow divider that is sack-like, rather than having a peripheral channel, and that uses a pair of deployment wires to deploy.

FIGS. 24–26 disclose embodiments of the flow divider 110 that are deployed by extending one or more preshaped deployment wires 146, 148 from within the catheter 1100. FIG. 24 shows an embodiment that employs two wires for deployment. This embodiment includes a nonporous film 140 surrounded by a peripheral tube 136 in which the deployment wires 146 and 148 reside. The deployment wires 146, 148 are coupled at one end to the distal end the catheter shaft at points 152. The deployment wires 146, 148 pass through one lumen, or alternatively two parallel lumens, from the proximal end 104 of the catheter 100 to the distal region of the catheter, and through deployment wire apertures 150 to the external surface of the distal region of the catheter 100. In the non-deployed state, the flow divider 110 is preferably folded tightly against the exterior of the catheter shaft 102 so that the outer diameter of the folded flow divider 110 is not much larger than the diameter of the catheter shaft 102. The flow divider 110 is deployed by pushing the proximal end of the deployment wires 146, 148 through lumens into the catheter shaft. As the deployment wires 146, 148 are extended from within the catheter 100, the deployment wires 146, 148 cause the flow divider 110 to deploy. The deployment wires 146, 148 are preferably preshaped to assume the desired configuration. FIG. 25 is a cross section view of the divider of FIG. 24 taken along line 25—25, and shows the deployment wires 146, 148 within the peripheral tube 136 of the deployed flow divider 110. In an alternate embodiment, as seen in FIG. 26, the flow divider 110 may be sack-like with the deployment wires 146, 148 preshaped to hold the flow divider 110 in an open or deployed configuration.

Figure 27:
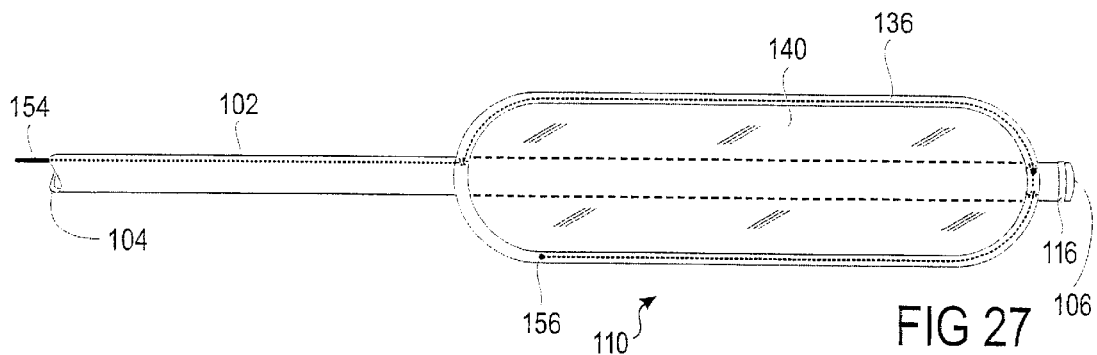
FIG. 27 shows an alternate embodiment of the flow divider of FIG. 24 that is deployed using only a single wire.

FIG. 27 discloses an alternate embodiment requiring only a single deployment wire 154. In this embodiment, the deployment wire 154 is not coupled to the distal end 106 of the catheter 100. Instead, the end of the deployment wire 154 is threaded through the peripheral tube 136 in a clockwise or counterclockwise direction. The deployment wire 154 is preferably preshaped to assume the desired configuration and includes a rounded end 156 for better tracking and to prevent the deployment wire 154 from puncturing the flow divider 110.

Figure 28:
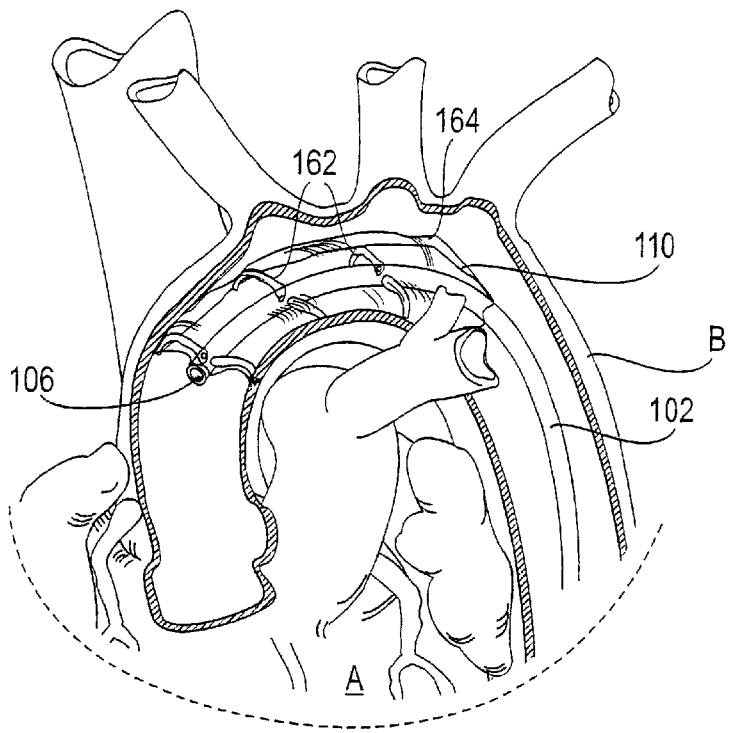
FIG. 28 shows a perspective view of an embodiment of the catheter of the invention wherein the flow divider comprises a shroud deployed by means of movable ribs.
Figure 29:
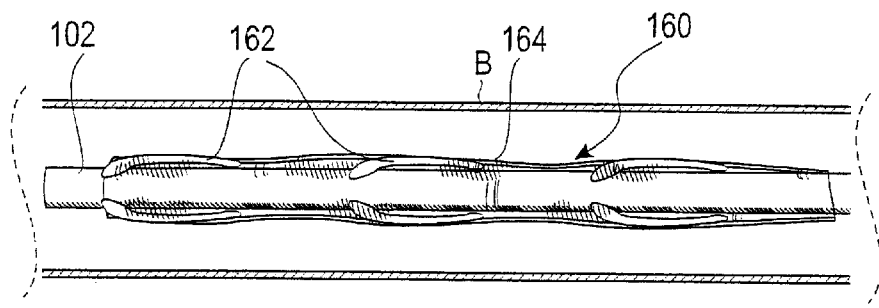
FIG. 29 shows a top view of the catheter of FIG. 28 in a collapsed configuration.
Figure 30:
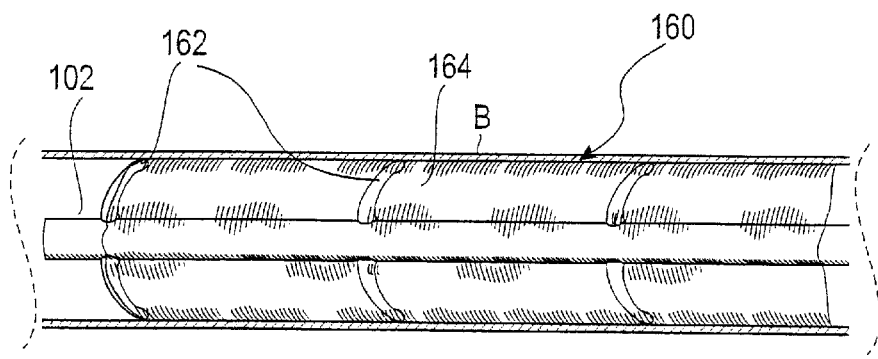
FIG. 30 shows a top view of the catheter of FIG. 28 in a deployed configuration.

FIG. 28 discloses a perspective view of an embodiment of the catheter of the invention wherein the flow divider 110 comprises a shroud 164 deployed by means of movable ribs or arms 162. The flow divider 110 seen in FIG. 28 comprises a plurality of mechanical pivot arms 162 with a film or web-like shroud 164 bonded to the catheter shaft 102 and the pivot arms 162. The pivot arms 162 may be mechanically extended, but in alternate embodiments, fluid pressure may be used to pivot the arms 162. In other alternate embodiments, the pivot arms 162 may instead be hollow tubes, which are extended by filling them with fluid under pressure. When the pivot arms 162 are extended, the shroud 164 unfolds, and the flow divider 110 is deployed. FIG. 29 shows the flow divider 110 of FIG. 28 in a collapsed or-undeployed state with the pivot arms 162 pivoted against the catheter shaft 102, and the shroud 164 folded against the catheter shaft 102. FIG. 30 shows a top view of the flow divider 110 in a deployed configuration. Once deployed, this embodiment of the flow divider 110 is used in the same way as the flow dividers previously described.

Figures 31, 32:
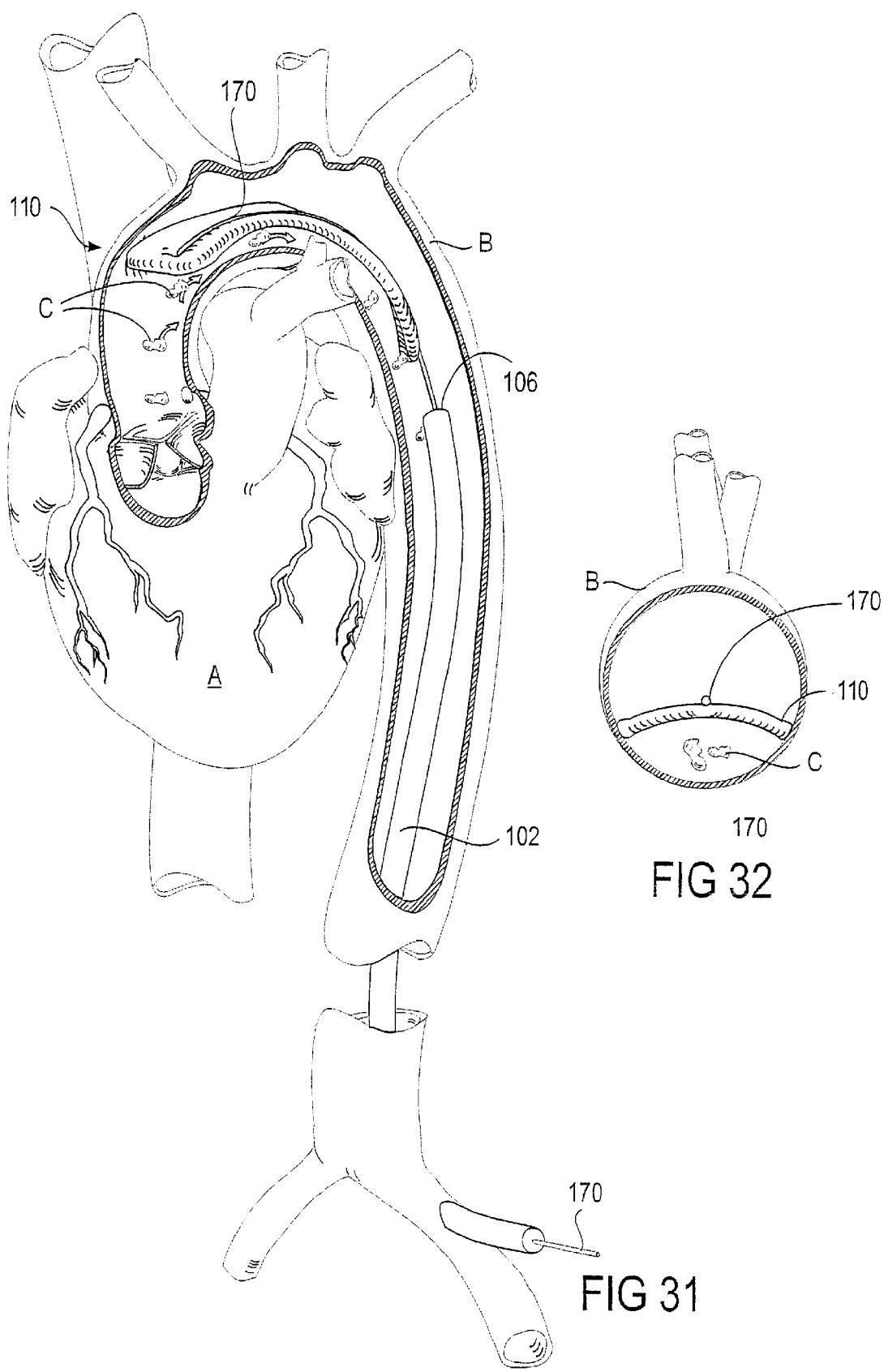
FIG. 31 shows a first embodiment of the flow divider of the invention deployed from a lumen within a catheter.
FIG. 32 shows a cross section of the flow divider and aorta of FIG. 31 taken transversely through the aorta.

All of the previously described flow divider 110 embodiments have been deployed from the external surface of the catheter shaft. However, in other embodiments, the flow divider 110 may be deployed from within one or more lumens in the catheter shaft. For example, FIG. 31 discloses a flow divider 110 deployed within an aorta B, and coupled to a deployment wire 170 that is extended from a lumen with an opening in the distal end 106 of the catheter shaft 102. The flow divider 110 is preferably comprised of a material or materials with a shape memory, so that the flow divider 110 will assume the desired configuration on release from the catheter shaft 102. Any known suitable materials may be used including, but are not limited to, elastomers, thermoplastic elastomers, polyvinylchloride, polyurethane, polyethylene, polyamides, polyesters, silicone, latex, and alloys or copolymers, and reinforced composites thereof. In some embodiments, the flow divider 110 may include lateral or branch stiffeners to assist the flow divider 110 in maintaining a desired configuration or shape. Perfusion of the arch vessels in this embodiment, may be provided by another perfusion source, such as a second catheter. FIG. 32 is a cross section view of the flow divider 110 of FIG. 31 taken transversely through the aorta B showing a preferred position of the flow divider 110 within the aorta B.

Figure 33:
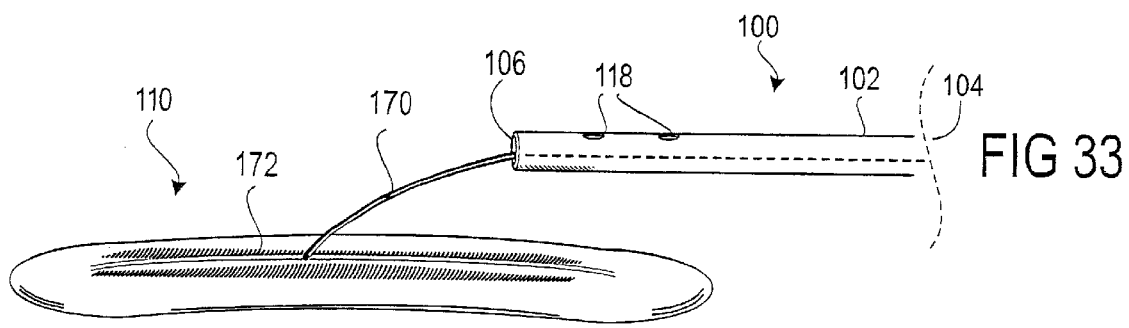
FIG. 33 shows a flow divider, having a flexible stiffening spine, deployed from within a lumen having an opening in the distal end of the catheter and coupled to a deployment wire at a point intermediate the ends of the spine.
Figure 34:
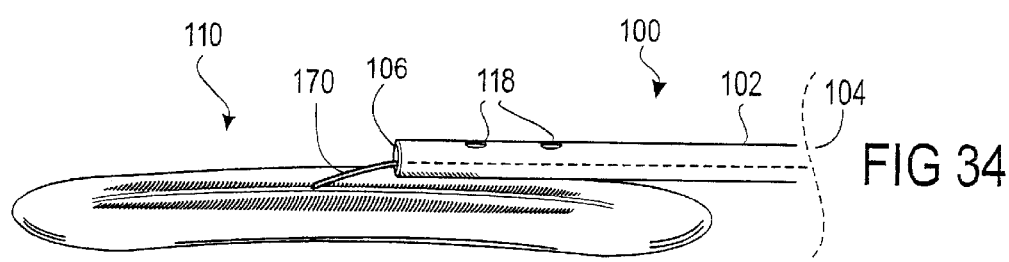
FIG. 34 shows the flow divider and catheter of FIG. 33 with the deployment wire retracted to the distal end of the catheter so that the catheter is positioned for perfusion of the arch vessels.
Figure 35:
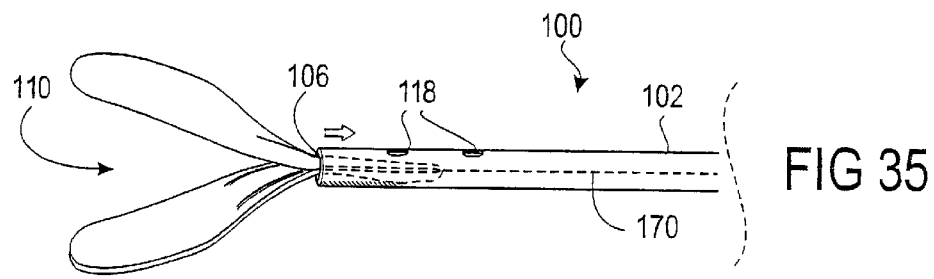
FIG. 35 shows the flow divider of FIG. 33 partially withdrawn into the catheter.
Figure 36:
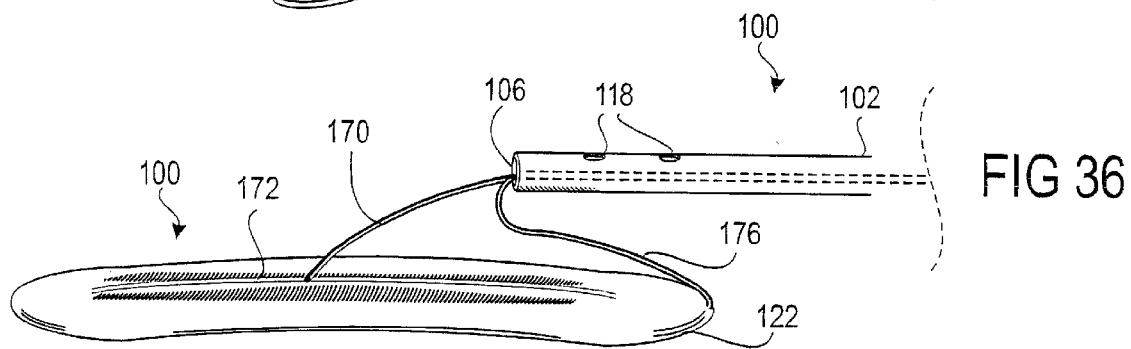
FIG. 36 shows an alternate embodiment of the flow divider of FIG. 33 with an additional withdrawal wire.
Figure 37:
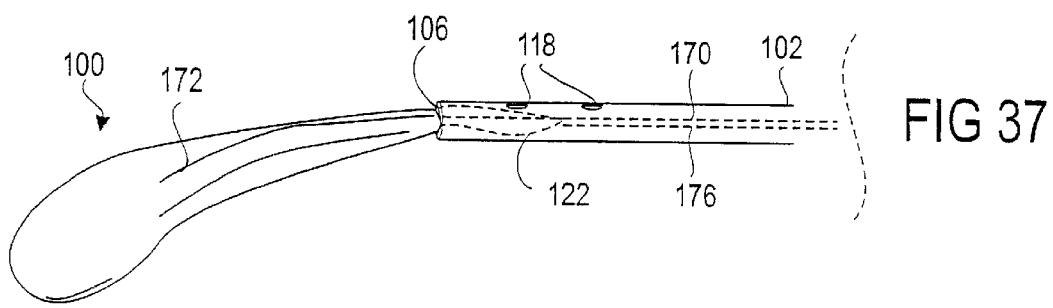
FIG. 37 shows the flow divider of FIG. 36 partially withdrawn into the catheter.

FIG. 33 illustrates an alternate embodiment of the flow divider 110 of FIG. 31. In this embodiment, the flow divider 110 includes a stiff spine 172 extending along the length of the flow divider 110 with a deployment wire 170 coupled to the spine 172 at a point intermediate the ends of the spine 172. The flow divider 110 may include additional stiffening structures if desired. The flow divider 110 may be used independently or it may be deployed through a catheter 100. The flow divider 110 is deployed by pushing the flow divider 110 out of a lumen having an opening near the distal end 106 of the catheter 100. The catheter 100 may then be advanced until the distal end 106 of the catheter 100 is proximate the point 174 at which the deployment wire 170 is coupled to the spine 172 of the flow divider 110, as shown in FIG. 34. The catheter 100 may include additional perfusion ports 118 near the distal end 106 of the catheter 100 to perfuse the region above the flow divider 110. FIG. 35 shows an embodiment of the flow divider 110 being withdrawn. In some embodiments withdrawal of the flow divider 110 may be accomplished by pulling the flow divider 110 into the lumen of the catheter 100. The flow divider 110 may bend at the connection point between the deployment wire 170 and the flexible spine 172. FIG. 36 shows an alternate embodiment including a tether wire 176 coupled to the proximal end 122 of the flow divider 110 nearest the catheter 100. In this embodiment, the catheter 100 need not be bent to be withdrawn. Instead, the flow divider 110 is withdrawn by pulling the tether wire 176. This aligns the end of the flow divider 110 with the opening of the lumen into which the flow divider 110 will be withdrawn, as seen in FIG. 37.

Figure 38:
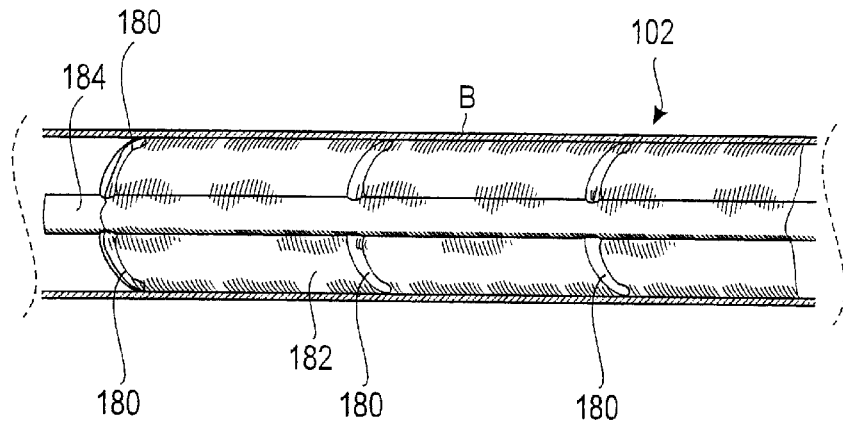
FIG. 38 shows a fully deployed flow divider similar in construction to the flow divider of FIG. 28, but that is deployed from within a lumen in a catheter shaft.
Figure 39:
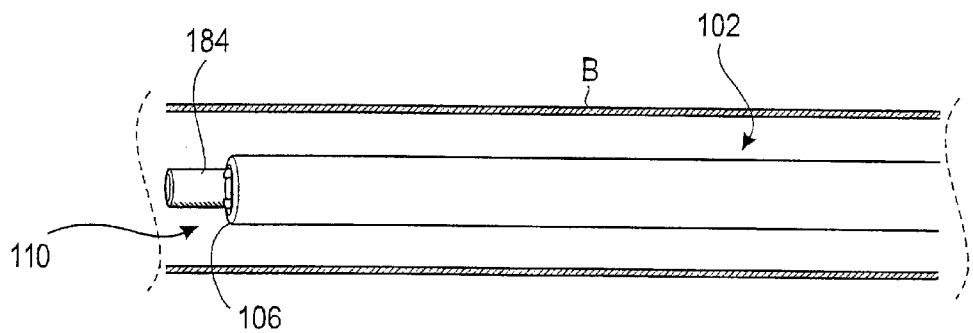
FIG. 39 shows the flow divider of FIG. 38 in an undeployed state within the catheter.
Figure 40:
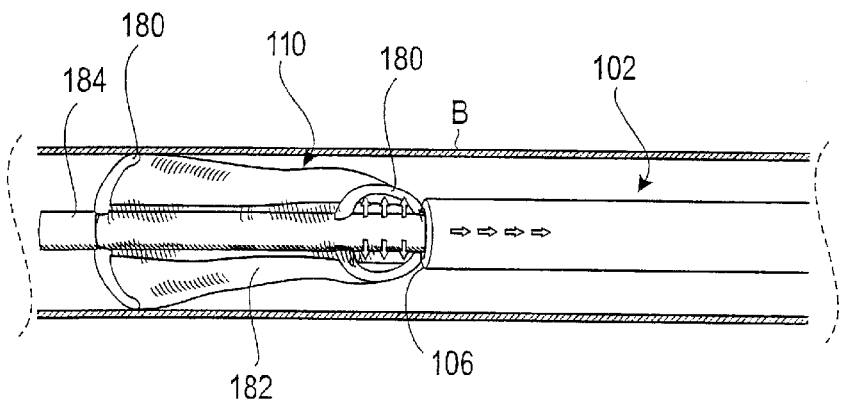
FIG. 40 shows the flow divider of FIG. 38 partially deployed.

FIGS. 38–40 illustrate an embodiment of the flow divider 110 comprising a plurality of flexible arms 180 extending from a spine or inner catheter 184 with a shroud or web 182 extending between the flexible arms 180. The flow divider 110 is deployed from a lumen within the catheter shaft 102 from an opening at the distal end 106 of the catheter shaft 102. FIG. 38 shows the flow divider 110 deployed within the aortic lumen B. The flexible arms 180 are arrayed extending outward from the shaft of the flow divider 110, supporting the shroud or web 182 between the extended flexible arms 180. FIG. 39 shows the flow divider 110 of FIG. 38 disposed in an undeployed state within the catheter shaft 102. FIG. 40 shows the flow divider 110 partially deployed from within the catheter shaft 102. As the flow divider 110 is pushed from the distal end 106 of the catheter 100, the flexible arms 180 spring outward, deploying the shroud or web 182 between the flexible arms 180. The flow divider 110 is withdrawn by pulling the flow divider 110 into the catheter shaft 102. The flexible arms 180 fold again, but in the opposite direction. In an alternate embodiment, the flow divider 110 may be coupled to the exterior surface of the catheter shaft 102, and have a sheath slid over the divider in its undeployed configuration. The divider may then be deployed by sliding the sheath along the catheter shaft 102 to expose the flow divider 110. In another alternative embodiment, the flexible arms 180 may be pivotally attached to the inner catheter 184, and the flow divider 110 may be mechanically deployed and retracted by deployment wires (not shown) within the inner catheter 184. In yet another alternative embodiment, the flexible arms 180 may be inflatable and deflatable to deploy and retract the flow divider 110.

FIGS. 41 and 42 illustrate an embodiment of the flow divider 110 comprising a flexible tongue that is folded back within the catheter shaft 102 and deployed using a deployment wire 186 to push the flow divider 110 out. Referring to FIG. 41, the proximal end of the flow divider 110 is coupled to the distal end 106 of the catheter shaft 102 at point 188. Deployment is accomplished by using a deployment wire 186 to push the flow divider 110 out of the lumen in the catheter shaft 102. The dotted lines 110' show intermediate positions of the flow divider 110 as it is deployed. FIG. 42 shows the flow divider 110 of FIG. 41 fully deployed and with the deployment wire 186 retracted. Once the deployment wire 186 is removed, the aorta above the upper surface of the flow divider 110 can be perfuse through the same lumen used by the deployment wire 186.

In one method of use, the aortic catheter 100 of any of the embodiments described above may be introduced into the patient's circulatory system through a peripheral artery access such as the femoral artery, by the percutaneous Seldinger technique, through an introducer sheath, or via an arterial cutdown. Referring more. specifically to FIG. 5, the catheter 100 is advanced up the descending aorta and across the aortic arch, under fluoroscopic or ultrasound guidance with the aid of a guidewire within the guidewire lumen 114. The aortic catheter 100 is advanced until the flow divider 110 is positioned in the aortic arch. This may be determined by reference to the location markers 116. The divider 110 is then deployed, dividing the aortic lumen into two flow channels. Using a multihead cardiopulmonary bypass pump or the like, perfusion of oxygenated blood is. started through the perfusion ports 118 to perfuse the flow channel above the flow divider 110, and thereafter to perfuse the arch vessels. Blood from the heart is directed through the flow channel below the flow divider 110. At the completion of the surgical procedure, and after the majority of embolic material has passed harmlessly beyond the arch vessels, the divider 110 is retracted or allowed to collapse. The aortic lumen is then no longer divided into two flow channels, and oxygenated blood is allowed to flow from the heart to the arch vessels. The patient is then weaned off the bypass, and the catheter 100 and other cannulas are withdrawn.

In an alternative method, a catheter embodiment configured for antegrade deployment, such as those shown in FIGS. 15 and 16, would be used similarly, except that access to the patient's circulatory system would be made through a central access by an aortotomy or incision directly into the ascending aorta. The aorta may be accessed through a median sternotomy or other thoracotomy using standard open-chest or minimally invasive surgical techniques.

Either method may be used with the heart beating or with the heart arrested, for example, by cardioplegic arrest. When used on an arrested heart, the method may include the additional steps of occluding the ascending aorta with a cross clamp or using an auxiliary flow control member, as shown in FIG. 13, and infusing a cardioplegic agent into the aortic root distal to the auxiliary flow control member through a lumen in the catheter or through a separate cannula, or into the coronary arteries via retrograde infusion.

Modification of the operational characteristics or procedures set forth above for use in vessels other than the aorta for perfusion of blood to branch vessels, or for use of other catheter configurations disclosed herein, are readily ascertainable by those skilled in the art in view of the present disclosure.

What is claimed is:

1. A method of providing selective flow within a blood vessel having a longitudinal axis and wherein a lumen is defined by a vessel wall, comprising the steps of:

(a) partitioning the lumen of a main vessel along said longitudinal axis such that portions of said vessel wall define adjacent flowpaths;

(b) establishing a first fluid flow through one of said flowpaths in fluid communication with at least one branch vessel; and (c) establishing a second fluid flow through another of said flowpaths in fluid communication with the main vessel.

2. The method of claim 1, wherein step (b) is carried out by:

providing said first fluid flow substantially free of emboli.

3. The method of claim 1, wherein step (b) is carried out by:

providing said first fluid flow of temperature conditioned fluid.

4. The method of claim 1, wherein step (b) is carried out by:

providing said first fluid flow of temperature conditioned blood.

5. The method of claim 1, wherein step (b) is carried out by:

providing a hypothermic conditioned blood.

6. The method of claim 1, wherein step (b) is carried out by:

providing a normothermic conditioned blood.

7. The method of claim 4, wherein step (b) is carried out by:

providing a hyperthermic conditioned blood.

8. The method of claim 1, wherein said second fluid flow is provided by a beating heart.

9. The method of claim 4, wherein said second fluid flow is provided through a heart.

10. The method of claim 4, wherein said second fluid flow is through a beating heart.

11. The method of claim 1, further comprising:

perfusing the first fluid flow through a first perfusion lumen and perfusing the second fluid flow through a second perfusion lumen.

12. The method of claim 11, further comprising:

perfusing the first fluid flow with hypothermic fluid and perfusing the second fluid flow with normothermic fluid.

13. The method of claim 11, further comprising:

perfusing the first fluid flow with normothermic fluid and perfusing the second fluid flow with normothermic fluid.

14. The method of claim 11, further comprising:

perfusing the first fluid flow with hyperthermic fluid and perfusing the second fluid flow with hyperthermic fluid.

15. A method of providing selective flow in a vessel comprising the steps of:

partitioning the lumen of the aortic arch such that a first portion of said vessel defines a first flow channel in communication with the aortic arch vessels and a second portion of said vessel defines a second flow channel adjacent to said first flow channel which bypasses the aortic arch vessels; and creating a temperature gradient between said first flow channel and said second flow channel.

16. The method of providing selective flow of claim 15, wherein the partitioning step is carried out by:

positioning a divider in an aorta.

17. The method of claim 15, further comprising the steps of:

maintaining a lower temperature in said first flow channel.

18. The method of claim 15, further comprising the steps of:

maintaining a higher temperature in said first flow channel.

19. The method of claim 15, further comprising the steps of:

maintaining a normothermic temperature in said first flow channel.

20. The method of claim 15, further comprising the steps of:

maintaining a hypothermic temperature in said first flow channel.

21. The method of claim 15, further comprising the steps of:

maintaining a hyperthermic temperature in said first flow channel.

22. A method of providing selective flow in a vessel comprising the steps of:

inserting an aortic divider into the vessel of a patient;

navigating said divider into an operative position within the aortic arch;

dividing the lumen of the aortic arch with said divider;

generating a first flow channel above said divider that is in fluid communication with the aortic arch vessels;

generating a second flow channel below said divider which bypasses the aortic arch vessels;

perfusing a first fluid from a first perfusion lumen into said first fluid flow channel; and perfusing a second fluid from a second perfusion lumen into said second fluid flow channel.

23. The method of providing selective flow in a vessel of claim 22, further comprising the step of:

creating a temperature gradient between said first flow channel and said second flow channel.

24. The method of providing selective flow in a vessel of claim 22, further comprising the step of:

creating a pressure gradient between said first flow channel and said second flow channel.

25. The method of providing selective flow in a vessel claim 22, further comprising the step of:

establishing a preferential flow path between said first flow channel and said second flow channel such that flow from said first flow channel is allowed to flow around said divider into said second flow channel and fluid from said second fluid flow channel is resisted from flowing into said first fluid flow channel.

* * * * *